(12) United States Patent
Rickard et al.

(10) Patent No.: US 10,806,341 B2
(45) Date of Patent: Oct. 20, 2020

(54) SYSTEMS AND METHODS FOR MONITORING EYE HEALTH

(71) Applicant: California Baptist University, Riverside, CA (US)

(72) Inventors: Matthew Rickard, Riverside, CA (US); Creed Jones, Riverside, CA (US)

(73) Assignee: California Baptist University, Riverside, CA (US)

(*) Notice: Subject to any disclaimer, the term of this patent is extended or adjusted under 35 U.S.C. 154(b) by 851 days.

(21) Appl. No.: 14/831,234

(22) Filed: Aug. 20, 2015

(65) Prior Publication Data

US 2016/0051144 A1    Feb. 25, 2016

Related U.S. Application Data

(60) Provisional application No. 62/039,847, filed on Aug. 20, 2014.

(51) Int. Cl.
| | |
|---|---|
| *A61B 3/16* | (2006.01) |
| *A61B 5/00* | (2006.01) |
| *A61B 5/07* | (2006.01) |
| *G01B 7/16* | (2006.01) |
| *G01M 5/00* | (2006.01) |

(Continued)

(52) U.S. Cl.
CPC ........... *A61B 3/16* (2013.01); *A61B 3/0008* (2013.01); *A61B 3/0025* (2013.01); *A61B 3/0083* (2013.01); *A61B 3/1241* (2013.01); *A61B 3/145* (2013.01); *A61B 5/0013* (2013.01); *A61B 5/076* (2013.01); *A61B 5/1116* (2013.01); *A61B 5/4842* (2013.01); *A61B 5/4884* (2013.01); *A61B 5/6803* (2013.01); *A61B 5/686* (2013.01); *A61B 5/6898* (2013.01); *A61B 5/7275* (2013.01); *G01B 7/18* (2013.01); *G01B 11/165* (2013.01); *G01M 5/0008* (2013.01); *G01M 5/0033* (2013.01); *G01M 5/0083* (2013.01); *A61B 2560/0214* (2013.01); *A61B 2560/0219* (2013.01); *A61B 2562/0219* (2013.01); *A61B 2562/0261* (2013.01); *A61B 2562/0266* (2013.01); *A61B 2562/164* (2013.01);

(Continued)

(58) Field of Classification Search
None
See application file for complete search history.

(56) References Cited

U.S. PATENT DOCUMENTS 5,812,240 A * 9/1998 Teraoka ............. A61B 3/145
                                                        351/206
6,019,472 A * 2/2000 Koester ............. A61B 3/125
                                                        351/219

(Continued)

OTHER PUBLICATIONS

Search Report & Written Opinion of PCT/US2015/046139, Authorized officer Blaine R. Copenheaver; Nov. 19, 2015.

*Primary Examiner* — Matthew Kremer
(74) *Attorney, Agent, or Firm* — Benjamin Diederich

(57) ABSTRACT

Systems and methods for monitoring eye health. The systems and methods monitor eye health by measuring scleral strain by way of an implantable monitor, a wearable monitor configured in eyeglasses, or an external monitor using a portable tablet computing device.

Certain embodiments of the strain monitor may be utilized to measure the strain on any surface to which it is attached, including, but not limited to, the skin of a patient or the surface of a structure such as a building or a bridge.

8 Claims, 17 Drawing Sheets

(51) Int. Cl.
*G01B 11/16* (2006.01)
*A61B 3/00* (2006.01)
*A61B 3/12* (2006.01)
*A61B 3/14* (2006.01)
*A61B 5/11* (2006.01)
*G16H 50/30* (2018.01)
*G16H 40/63* (2018.01)

(52) U.S. Cl.
CPC ......... *G01B 2210/58* (2013.01); *G16H 40/63* (2018.01); *G16H 50/30* (2018.01)

(56) References Cited

U.S. PATENT DOCUMENTS

| | | |
|---|---|---|
| 6,110,110 A | 8/2000 | Dublin, Jr. et al. |
| 2002/0113943 A1* | 8/2002 | Trajkovic ............... G02B 7/102 351/209 |
| 2005/0165321 A1* | 7/2005 | Fischell ............... A61B 5/0452 600/515 |
| 2007/0055222 A1 | 3/2007 | Hohla et al. |
| 2009/0203985 A1 | 8/2009 | Ehrecke |
| 2010/0286498 A1* | 11/2010 | Dacquay ................. A61B 3/16 600/398 |
| 2012/0238857 A1 | 9/2012 | Wong et al. |
| 2012/0293773 A1 | 11/2012 | Publicover et al. |
| 2013/0030257 A1* | 1/2013 | Nakata ................. A61B 5/0507 600/301 |
| 2013/0041245 A1 | 2/2013 | Cerboni |
| 2014/0055567 A1 | 2/2014 | Dyer |
| 2014/0055746 A1* | 2/2014 | Nistico ................ A61B 3/0008 351/206 |
| 2014/0228668 A1 | 8/2014 | Wakizaka et al. |
| 2015/0206008 A1* | 7/2015 | Border ................. A61B 5/1171 351/206 |

* cited by examiner

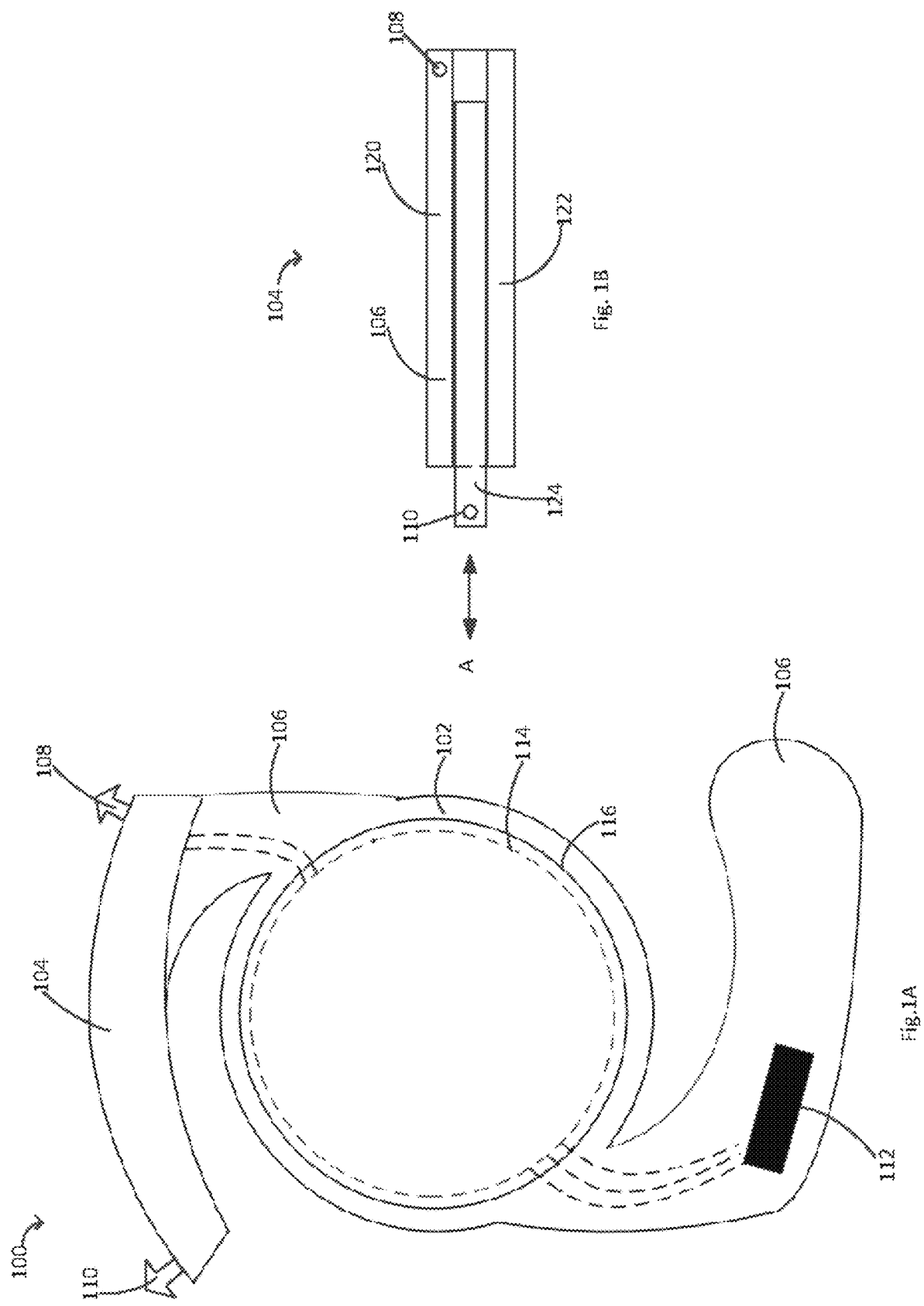

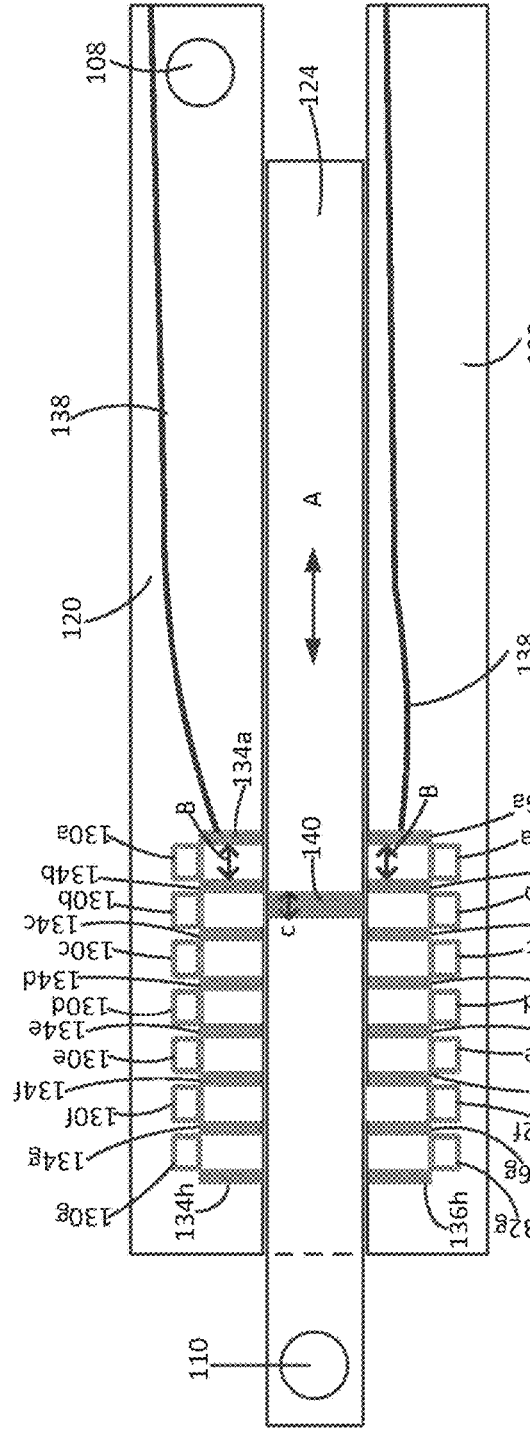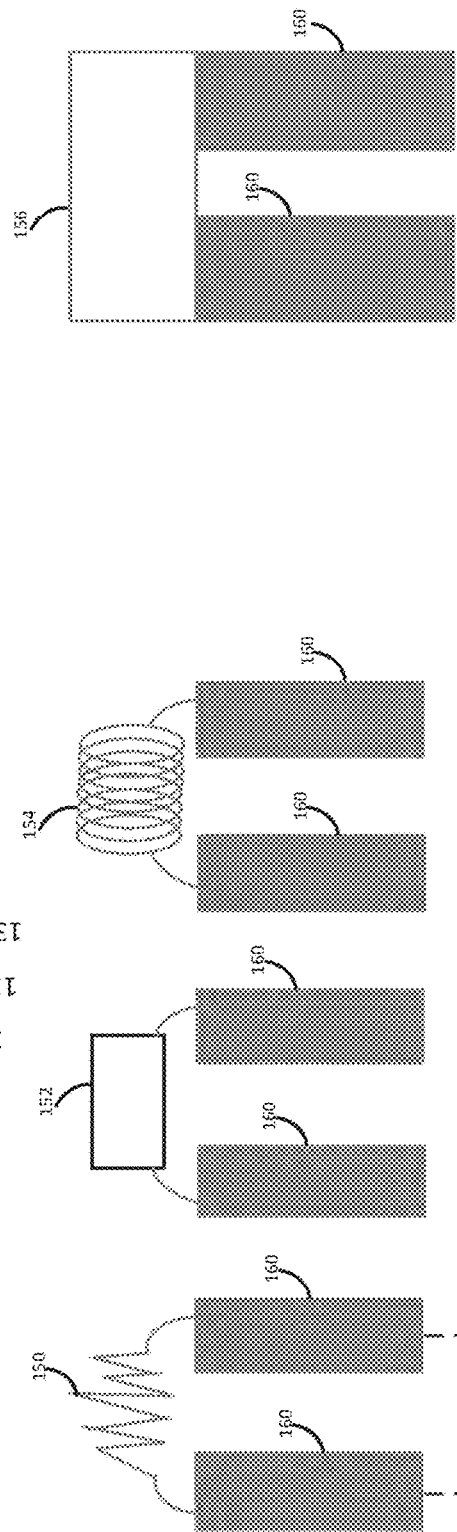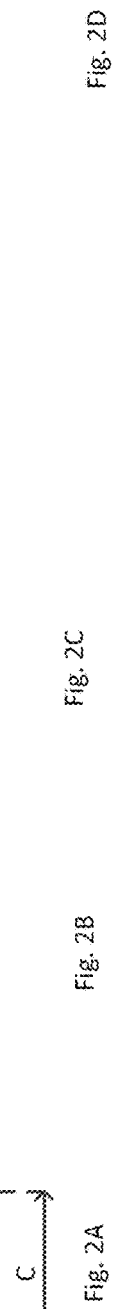

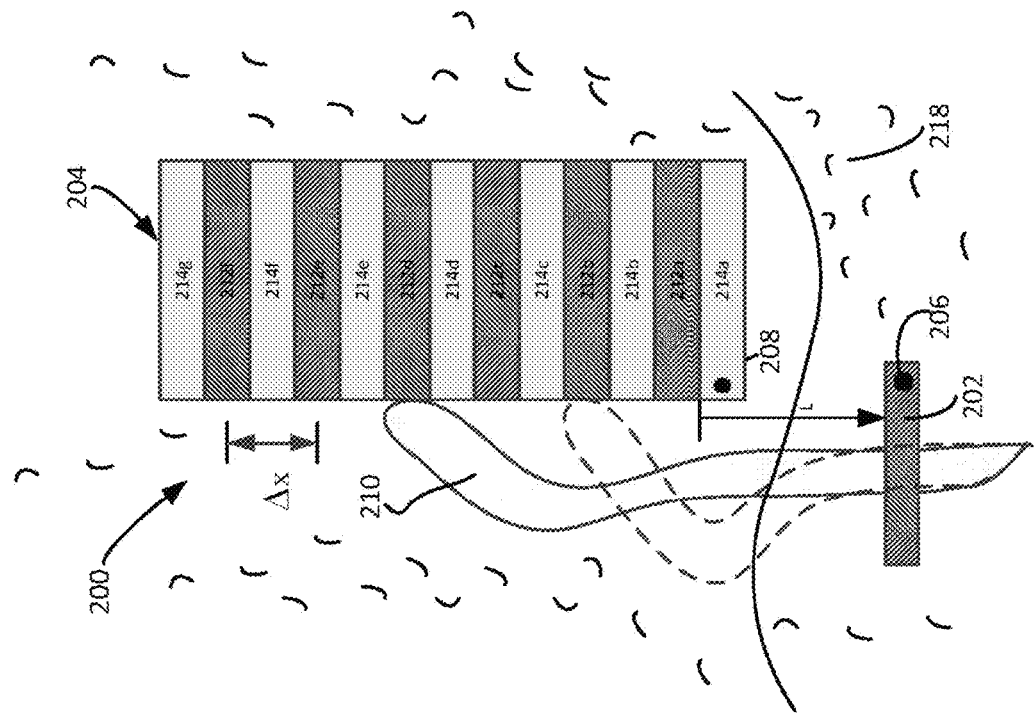
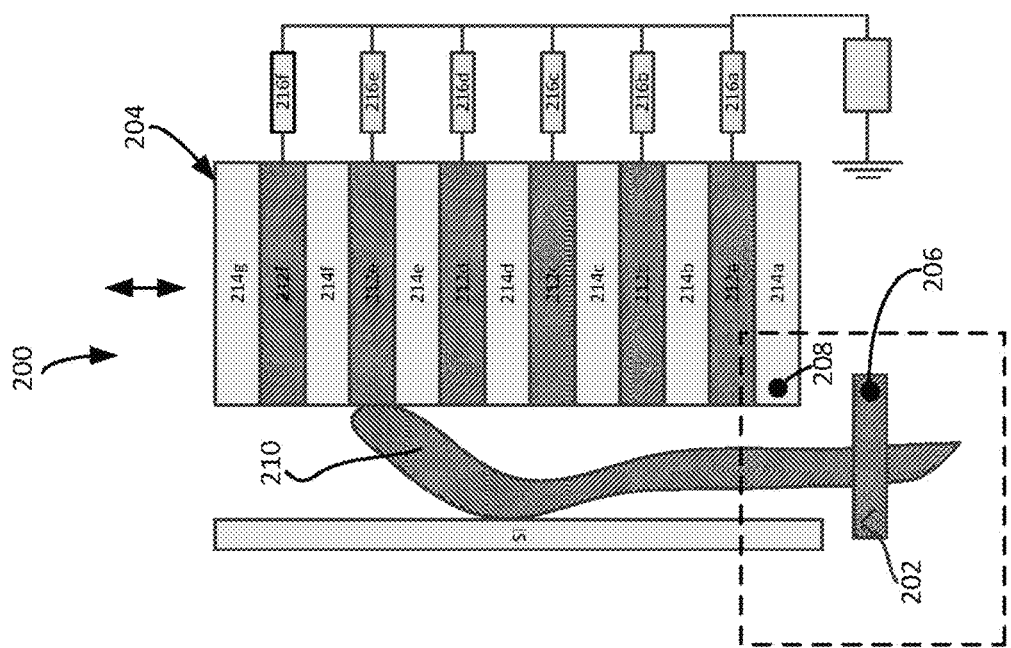
Fig. 3B
Fig. 3A

SYSTEMS AND METHODS FOR MONITORING EYE HEALTH

CROSS-REFERENCE TO RELATED APPLICATIONS

This application claims the benefit of U.S. Provisional Application No. 62/039,847, filed on Aug. 20, 2014, the teachings of which are expressly incorporated by reference.

STATEMENT RE: FEDERALLY SPONSORED RESEARCH/DEVELOPMENT

Not Applicable

FIELD OF THE INVENTION

This application relates generally to strain monitoring devices. More particularly, this application relates to implantable strain monitoring devices for measuring scleral strain, wearable imaging devices for measuring scleral strain, external tablet-based imaging devices for measuring scleral strain, and strain monitoring devices for measuring the strain of a surface to which they are attached.

BACKGROUND OF THE DISCLOSURE

Glaucoma is an ocular disorder characterized by excessive intraocular pressure (IOP), which causes damage to the optic nerve and can lead to permanent loss of vision. It is estimated that over 2.2 million Americans have glaucoma but only half of those are aware of it. Glaucoma is the second leading cause of blindness in the world. Current methods for monitoring patients at risk for glaucoma involve intermittent measurements of IOP on an in-patient basis, based on applied pressure and deformation of the eyeball. There also exist devices which attempt to continuously monitor IOP, for example using a pressure sensor which is implanted in the aqueous chamber of the eye to directly measure IOP. Other methods utilize a strain gauge embedded in a contact lens to indirectly measure IOP. These prior methods are inconvenient, expensive and measure IOP via a pressure sensor on the surface based on the slight motion of a foreign, rigid surface that does not record unrestricted motion of the cornea or sclera.

It has been found that scleral strain correlates to, and provides additional information to, IOP. As such, it is desired to have systems and methods for measuring IOP and/or scleral strain in a non-invasive fashion.

SUMMARY OF THE INVENTION

In one embodiment, disclosed herein are systems for monitoring eye health, the systems comprising: a scleral strain monitor adapted to be implanted in an eye, the scleral strain monitor comprising a sensor configured to measure electrical resistance between two electrical conductors, and to generate a signal representing said electrical resistance, and a transmitter configured to transmit the signal; and a reader adapted to be located outside the eye, the reader being configured to receive information transmitted by the transmitter.

In another embodiment, disclosed herein are systems for monitoring structural fatigue in constructions such as buildings or bridges that can undergo minute levels of strain. These systems comprise a sensor configured to measure electrical resistance between two electrical conductors and to generate a signal representing said electrical resistance, a transmitter configured to transmit the signal, and a reader configured to receive information transmitted by the transmitter.

In yet another embodiment, disclosed herein are systems for monitoring eye health, that comprise: a scleral strain monitor comprising a) a wearable pair of eyeglasses comprising i) one or more image sensors, ii) a CPU, iii) a memory storage device, iv) one or more connecting wires, and v) and a power source; and b) at least one preselected target region on or in the sclera, wherein the CPU receives images from the image sensors and then transmits the images to the memory storage device. Also disclosed are methods of using the disclosed systems to determine the health of an eye of an individual.

In a further embodiment, disclosed herein are systems for monitoring eye health comprising a portable tablet device having a camera, a lens assembly connectable to the camera of the portable tablet, and a comfort pad attached to the portable tablet for maintaining a distance from the tablet and a patient utilizing the system.

BRIEF DESCRIPTION OF THE DRAWINGS

FIG. 1A is a front view of an implant including a sensor according to an embodiment.

FIG. 1B is a top view of the sensor shown in FIG. 1A.

FIG. 1C is an enlarged view of the sensor shown in FIG. 1B.

FIG. 2A is schematic drawing of an example of a resistor configured for use in an embodiment.

FIG. 2B is schematic drawing of another example of a resistor configured for use in an embodiment.

FIG. 2C is schematic drawing of another example of a resistor configured for use in an embodiment.

FIG. 2D is schematic drawing of another example of a resistor configured for use in an embodiment.

FIG. 3A is a schematic drawing showing a top view of an example of a sensor configured in accordance with another embodiment.

FIG. 3B is a schematic drawing showing another view of the sensor shown in FIG. 3A.

DETAILED DESCRIPTION OF THE EMBODIMENTS

Figure 3C:
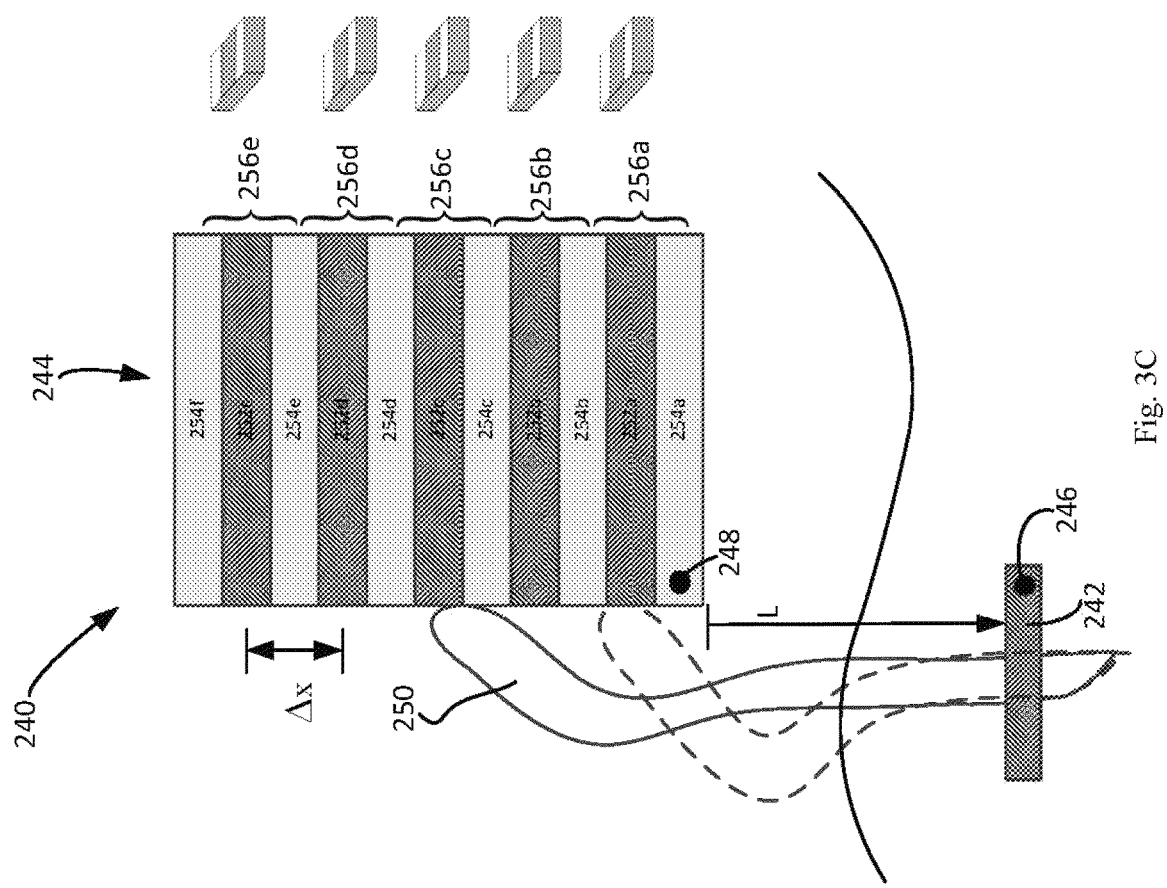
FIG. 3C is a schematic drawing showing a top view of an example of a sensor configured in accordance with a further embodiment.

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

Sensor Based System for Monitoring Eye Health:

A system for monitoring eye health comprising: a scleral strain monitor adapted to be implanted in an eye, the scleral strain monitor comprising a) a sensor configured to measure electrical resistance between two electrical conductors, and to generate a signal representing said electrical resistance;

b) a transmitter configured to transmit the signal; and c) a reader adapted to be located outside the eye, the reader being configured to receive information transmitted by the transmitter.

A method of monitoring eye health comprising: providing a scleral strain monitor adapted to be implanted in an eye, the scleral strain monitor comprising a) a sensor configured to measure electrical resistance between two electrical conductors, and to generate a signal representing said electrical resistance, the sensor comprising at least first and second anchor members being spaced apart from one another, the first and second anchor members being adapted to be secured to respective first and second anchor locations on or in a ciliary body;

b) a transmitter configured to transmit the signal; and c) a reader adapted to be located outside the eye for receiving information transmitted by the transmitter.

The features, aspects and advantages of the developments will now be described with reference to the drawings of several embodiments, which are intended to be within the scope of the invention herein disclosed. These and other embodiments will become readily apparent to those skilled in the art from the following detailed description of the embodiments having reference to the attached figures, the invention not being limited to any particular embodiment(s) disclosed.

Although the exact etiology of glaucoma remains unknown, it is generally understood that excessively high intraocular pressure (IOP), which may be caused by a flow obstruction in the trabecular meshwork, causes damage to the optic nerve and leads to permanent loss of vision. Accordingly, conventional methods for preventing the onset and progression of glaucoma all involve monitoring patients for high IOP, typically through intermittent measurements performed on an in-patient basis. More recent approaches propose continuous monitoring of IOP, either through an implantable IOP sensor or a contact lens IOP sensor. Yet it has been observed that even patients with statistically normal IOP measurements can develop glaucoma. Still other patients can show elevated levels of IOP while exhibiting no signs of glaucoma, even over extended observation periods. This may occur as a result of the fact that the biomechanical properties of the tissues involved can vary significantly from patient to patient, creating different responses to varying IOPs.

In embodiments, an entirely different parameter than IOP—scleral strain—is the focus of glaucoma prevention and monitoring efforts. By measuring mechanical strain at the surface of the sclera, instead of (or in addition to) intraocular pressure, embodiments provide a more accurate indicator of glaucoma risk which takes into account the biomechanical characteristics of each patient's ocular tissues. Embodiments provide a strain sensor which is anchored to two or more discrete points or regions on or in the sclera (or tissues adjacent to the sclera such as the ciliary body) and which is highly elastic in between those points, so as configured to provide an accurate indication of scleral strain in otherwise unrestricted ocular tissues.

With reference now to FIG. 1A, a front side view of an implant 100 forming part of a system for measuring eye health is shown. In the embodiment illustrated in FIG. 1A, the implant 100 includes an intraocular lens (IOL) 102 and a strain sensor 104 connected to the IOL 102. In some embodiments, the IOL 102 includes one or more haptics 106. In some embodiments, the implant 100 has a major dimension or length (from the top to the bottom as shown in FIG. 1A) between about 10 and 15 mm, or a length less than or greater than either of these numbers. For example, in some embodiments, the implant 100 has a length of about 13 mm. In some embodiments, the implant 100 has a minor dimension or width (from side to side as shown in FIG. 1A) of between about 5 and 10 mm, or a length less than or greater than either of these numbers. For example, in some embodiments, the implant 100 has a width of about 6 mm.

In some embodiments, the sensor 104 is formed separately from and connected to one of the haptics 106, while in other embodiments (as illustrated in FIGS. 1A and 1B), all or part of a haptic 106 forms a portion of the sensor 104. In some embodiments, the sensor 104 includes a proximal anchor member 108 and a distal anchor member 110 that are spaced apart from one another along the length of the haptic 106 (or along the circumference of the eye, as implanted). The anchor members 108, 110 are each configured to securely attach to separate areas on or in the sclera (or ciliary body) of the eye when the IOL 102 is implanted. In some embodiments, the anchor members 108, 110 are spaced apart by a distance of about 5, 6, 7, 8, 9, 10, 11, 12, 13, 14, or 15 mm, or a distance less than, greater than, or within a range defined by any of these numbers.

In some embodiments, the implant 100 further includes a circuit board 112, which includes a data logger and/or microprocessor to store, wirelessly send, and/or process the data measured from the sensor 104, and which, in certain embodiments, is connected to the sensor 104 by an electrical circuit 114. In some embodiments, the circuitry in 112 is also used to harvest wireless energy, such as that from an external unit that sends the implant energy and receives the implant's data. In some embodiments, the implant 100 also includes an antenna coil 116 to transmit and receive data measured from the sensor or processed by a microprocessor. In certain embodiments, the circuit 114 and the coil 116 are disposed so as not to impede vision once the implant 100 is implanted.

Various configurations of a strain sensor 104 may be used with the implant 100. The strain sensors 104 comprise different sensor configurations and different sensor locations in the various embodiments. In these embodiments, depending on the anatomy of the patient, the nature of the disease, and the preference of the healthcare practitioner, a combination of the sensor configuration and sensor location can be used.

FIG. 1B shows a top view of one embodiments of the strain sensor 104 and better illustrates the relative locations of the proximal anchor member 108 and the distal anchor member 110. The strain sensor 104 includes a first fixed member 120 (which, in the illustrated embodiment, is formed by a portion of the haptic 106), a second fixed member 122, and a movable member 124, which is disposed between the first and second fixed members 120, 122. In some embodiments, the fixed members 120, 122 and the movable member 124 are rigid. The proximal anchor member 108 is optionally disposed on, extends from, or forms part of the first fixed member 120 such that it is optionally secured to a first location on or in the sclera. The distal anchor member 110 is optionally disposed on, extends from, or forms part of the movable member 124 such that it is optionally secured to a second, spaced-apart location on or in the sclera.

In some embodiments, the fixed members 120, 122 and the movable member 124 are encapsulated in or otherwise disposed in a highly elastic material (for example having a Young's Modulus equal to or lower than that of the ocular tissue(s) to which the anchor members 108, 110 are secured) such that the anchor members 108, 110 move freely with respect to one another, at least in the direction indicated by arrow A. For example, in some embodiments, the fixed members 120, 122 and the movable member are encapsulated in silicone having a suitably low Young's Modulus. In some embodiments, the movable member 124 are disposed in a fluid, such as silicone gel, Viscoat® fluid available from Alcon Laboratories, or a balanced salt solution (BSS), which can be surrounded by an encapsulation material such as silicone. By such a configuration, once the anchor members 108, 110 are secured to the sclera, the distal anchor member 110 (and the movable member 124 to which it is connected) moves away from and/or back toward the proximal anchor member 108 as the sclera expands or contracts and the scleral strain is measured. In some embodiments, the encapsulated fluid serves to back fill in any voids generated by the motion of the member 124 relative to members 120, 122.

In embodiments, the anchor members 108, 110 has any configuration suitable for anchoring at least two discrete points or regions of the sensor 104 to two discrete points or regions on or in the sclera. For example, in some embodiments, the anchor members are rigid spikes configured to at least partially penetrate and anchor in ocular tissues. In other embodiments, the anchor members are discrete points or regions disposed, respectively, on fixed and movable portions of the sensor which are configured to be secured to the ocular tissues with biocompatible glue such as, for example, fibrin glue. In still other embodiments, the anchor members are discrete points, regions, or openings disposed, respectively, on fixed and movable portions of the sensor which are configured to be secured to the ocular tissues with sutures.

FIG. 1C shows a more detailed top view of the embodiment of the strain sensor 104 that was shown in FIG. 1B, and illustrates one possible arrangement of resistors 130 in the strain sensor 104. As illustrated in FIG. 1C, the first fixed member 120 includes a plurality of resistors 130(a), 130(b), 130(c), 130(d), 130(e), 130(f), and 130(g) connected in series to a plurality of conductors 134(a), 134(b), 134(c), 134(d), 134(e), 134(f), 134(g), and 134(h), which can be exposed along a surface of the first fixed member 120. Each of the conductors 134 are spaced apart by a distance B. The second fixed member 122 includes a plurality of resistors 132(a), 132(b), 132(c), 132(d), 132(e), and 132(f), and 132(g) connected in series to a plurality of conductors 136(a), 136(b), 136(c), 136(d), 136(e), 136(f), and 136(g), and 136(h), which are exposed along a surface of the second fixed member 122. Each of the conductors 136 is also spaced apart by a distance B and disposed opposite each of the conductors 134. Each set of conductors 134 and 136 is connected to the circuit 114 via at least one wire 138. The movable member 124 includes a connecting bar 140 having a width C. The connecting bar 140 is exposed at opposing surfaces of the movable member 124 such that it is configured to contact a different pair of resistors 130, 132 when the movable member 124 is in different lateral positions with respect to the fixed members 120, 122. In this way, as the sclera expands or stretches, the connecting bar 140 moves with the movable member 124 and closes the circuit between a different set of resistors 130, 132. For example, when the connecting bar 140 is in a position to connect conductors 134(c) and 136(c), the circuit 114 measures a resistance including resistors 130(a), 130(b), 132(a), and 132(b). Thus, a different level of resistance measured by the sensor 104 correlates to a different distance between anchor members 108 and 110 and, accordingly, to a different amount of scleral strain. In some embodiments, the width C of the connecting bar 140 is roughly the same as the distance B between each of the conductors 134, 136. In other embodiments, the width C of the connecting bar 140 is slightly less than the distance B between each of the conductors 134, 136, so as to avoid noise caused by slight motion of the sensor 104 or of the sclera. In some embodiments, connecting bar 140 is spring loaded such that it is flexed into a state prior to assembly that causes it to naturally push against conductors 134 and 136, ensuring proper electrical contact.

In this way, embodiments provide accurate measurements regarding scleral strain without necessarily requiring precise measurements of resistance, because any significant increase or decrease in resistance correlates to a specific change in the distance between (i.e, displacement of) the anchor members 108, 110. Put another way, embodiments provide accurate indications of scleral strain without requiring calibration of the sensor with respect to measurements of resistance. Thus, embodiments offer healthcare practitioners and patients confidence in strain readings even years after implantation.

In some embodiments, either or both of the fixed members 120, 122 are formed from any suitable rigid material, including, for example and without limitation, silicon. The resistors 130, 132 and the conductors 134, 136 are formed or embedded in the material forming the fixed members, with insulating material disposed so as to electrically isolate neighboring conductor/resistor sets from one another. In some embodiments, the movable member 124 is formed from silicon or any other suitable rigid material. The connecting bar 140 is formed or embedded in the material forming the movable member.

Although the embodiment illustrated in FIG. 1C includes seven resistors in each fixed member for purposes of illustration (i.e., seven pairs or "stages" of resistors, with fourteen resistors overall), embodiments can include any number and arrangement of resistors suitable for their intended purpose. For example and without limitation, embodiments can include 20, 40, 60, 80, 100, 120, 140, 160, 180, 200, 220, 240, 260, 280, 300, 400, or 500 discrete resistors, or a number of resistors less than, greater than, or within a range defined by any of these numbers. The resistors can be arranged in a single row (with each subsequent resistor in the row corresponding to a "stage"), arranged in pairs (with each pair of resistors corresponding to a "stage"), or arranged in any other configuration suitable for their intended purpose. For example, in some embodiments, the resistors need not be arranged in a straight line or even in the same plane; instead, the resistors can be arranged in a curvilinear pattern or in coplanar or non-coplanar arrangements. Further, although the embodiment illustrated in FIG. 1C shows two rows of resistors 130, 132, some embodiments can include only a single row of resistors and a single conducting electrode. In such an embodiment, either the row of resistors or the conducting electrode can be movable with respect to the proximal anchor member, and the distal anchor member can be disposed on the movable portion.

Figure 8B:
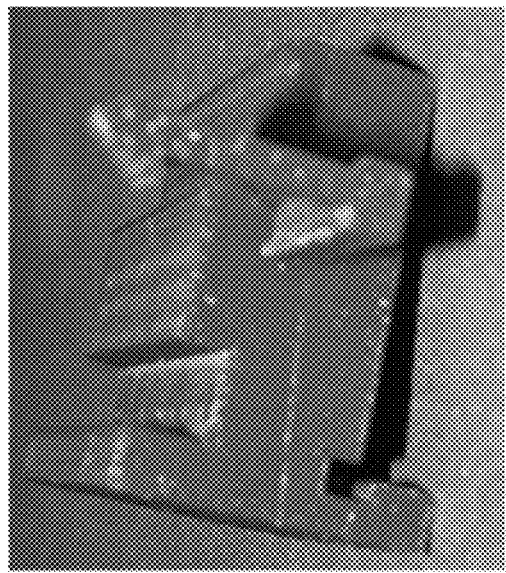
FIG. 8B is a side view of an example of a movable member of the sensor.
Figure 8A:
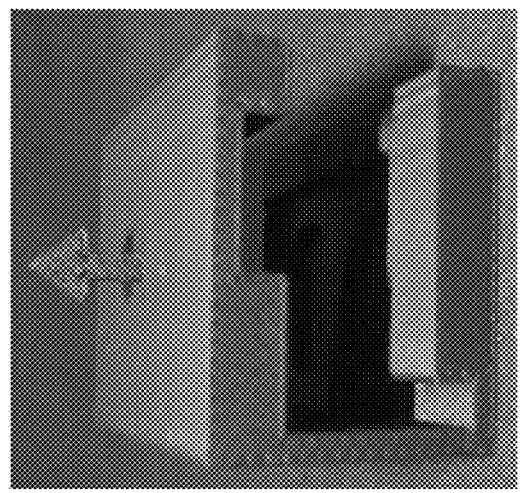
FIG. 8A is a side view of an example of a first fixed member of the sensor.

FIGS. 8A-8B show a detailed side view of the embodiment of a first fixed member 120 and a movable member 124.

Sclera strain levels indicative of glaucoma risk are expected to be on the order of about 1%. Accordingly, in some embodiments, the sensor 104 is configured to measure and/or record strain values of between about 0 and about 2%, 4%, 6%, 8%, 10%, or more, or a strain value less than, greater than, or within a range defined by any of these numbers. In some embodiments, the sensor 104 is configured to measure and record strain values of between about 1% and 7%. In some embodiments, the sensor 104 is configured to measure and/or record strain in increments of about 0.01%, 0.02%, 0.04%, 0.06%, 0.08%, 0.1%, 0.12%, 0.14%, 0.16%, 0.18%, 0.2%, 0.3%, 0.4%, 0.5%, 0.6%, 0.7%, 0.8%, or 0.8%, or 1%, or in increments less than, greater than, or within a range defined by any of these numbers. For example and without limitation, in one embodiment, the resistors 130, 132 are arranged so that each stage (or, each increase or decrease in measured resistance) corresponds to a change in scleral strain of approximately 0.01%.

In some embodiments, the spacing B between each of the conductors 134, 136 is any distance suitable for the intended purpose. For example and without limitation, the distance B between each of the conductors 134, 136 is about 0.001 mm, 0.005 mm, 0.01 mm, 0.05 mm, 0.1 mm, 0.2 mm, 0.3 mm, 0.4 mm, 0.5 mm, or a distance less than, greater than, or within a range defined by any of these numbers. Likewise, the width C of the connecting bar 140 is any width suitable for its intended purpose. For example and without limitation, the width C is about or slightly less than 0.001 mm, 0.005 mm, 0.01 mm, 0.05 mm, 0.1 mm, 0.2 mm, 0.3 mm, 0.4 mm, 0.5 mm, or a width less than, greater than, or within a range defined by any of these numbers. For example and without limitation, in one embodiment, a sensor 104 includes two rows of 25 resistors each, with the resistors in each row spaced apart by about 0.4 mm, so as to span a length of approximately 10 mm.

In some embodiments, each resistor 130, 132 has the same resistance, such that connection of each additional resistor 130, 132 in series results in roughly the same incremental increase in resistance. For example, in one embodiment, each resistor 130, 132 has a resistance of approximately 100 ohms. In other embodiments, each resistor is configured with a different resistance, for example such that connection of each additional resistor 130, 132 in series results in a more widely varying change in resistance. In some embodiments, the resistors in each set 130, 132 has an increasingly higher (i.e., graduated) level of resistance so as to reflect a marked difference between each connecting location, thereby minimizing the effect of minor fluctuations in resistance, minor movements of the sclera caused by motion of the patient, or other noise. For example and without limitation, one or both of the first resistors 130($a$), 132($a$) can have a resistance of about 10 ohms, one or both of the second resistors 130($b$), 132($b$) can have a resistance of about 100 ohms, one or both of the third resistors 130($c$), 132($c$) can have a resistance of about 1000 ohms, and so forth. In some embodiments, the level of resistance is such that it approximates a level of displacement of equal value (in different units). For example, the physical separation of each stage might be 10 microns and the increase in resistance from one stage to the next can be 10 kilo-ohms, requiring no computation for converting resistance changes to physical displacement.

Further, although the embodiment illustrated in FIG. 1C shows each row of resistors 130, 132 connected in series, some embodiments include resistors which are connected in parallel instead of in series. In such an embodiment, each resistor is configured with a different and possibly unique resistance (which can be increasing, decreasing, or randomly varied along the array of resistors) such that a particular resistance measurement corresponds to a particular displacement of the fixed and movable members and a corresponding level of strain.

In some embodiments, the sensor 104 is configured to provide an indication of IOP in addition to scleral strain. For example, some embodiments incorporate a transfer function which relates measured resistance and/or strain to IOP, based on an initial calibration of the IOP measurement. In some such embodiments, the resistors 130, 132 are arranged so that each stage (or, each increase or decrease in measured resistance) corresponds to a change in IOP of roughly 0.5 mm Hg. For example, in one embodiment, an implant 100 includes 200 discrete resistors arranged in 100 pairs or stages, with each stage spaced apart such that the sensor is configured to measure IOPs from about 0 to about 50 mm Hg.

The sensor 104 and its components are formed in any suitable fashion. For example, in some embodiments, the sensor 104 is formed using MEMS manufacturing methods, including, for example and without limitation, depositing layers or areas of conductive material (such as gold) on or in layers or areas of silicon.

FIGS. 2A-2D illustrate examples of various types of resistors that are used in embodiments. For example and without limitation, FIG. 2A shows a wire resistor 150 having a zig-zag configuration connected to conductors 160. In one embodiment, the wire resistor 150 includes a 1 micron wire in a zig-zag configuration having dimensions of approximately 0.1 mm by 0.1 mm. In some embodiments, resistors are formed by wires of different diameters or of different lengths. In some embodiments, each wire is coated with insulating material or otherwise insulated from neighboring wires. FIG. 2B shows an off-the-shelf resistor 152, which can be, for example, a ROHM 03015 chip resistor (ROHM Co., Ltd. Kyoto, Japan), which is 0.3 mm by 0.15 mm by 0.10 mm or size 01005 resistors available from Topline Corporation of Milledgeville, Ga. FIG. 2C shows another wire resistor 154 having a coil configuration connected to conductors 160. FIG. 2D shows still another resistor 156 which is formed from doped silicon, and which is connected to conductors 160. For example, in some embodiments, the fixed members 120, 122 is formed from silicon, and the resistors are formed by doping certain portions of the silicon to form resistive elements.

Figure 7B:
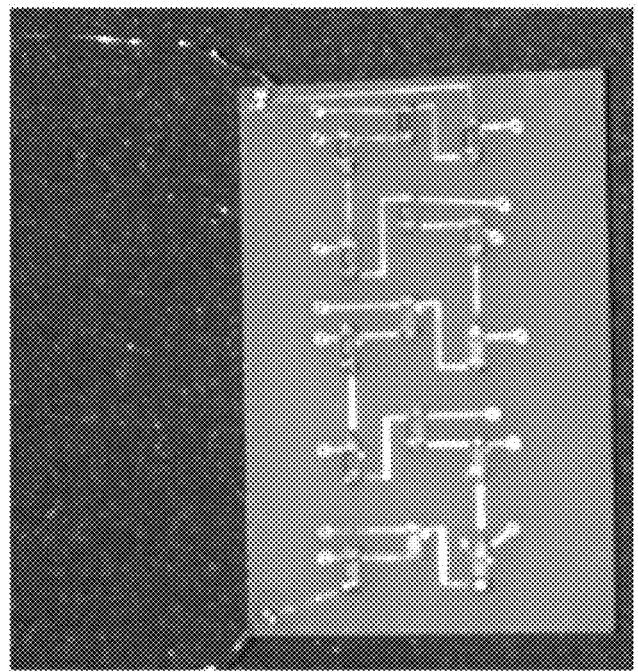
FIG. 7B is a schematic of an example of a resistor configured for use in an embodiment.
Figure 7A:
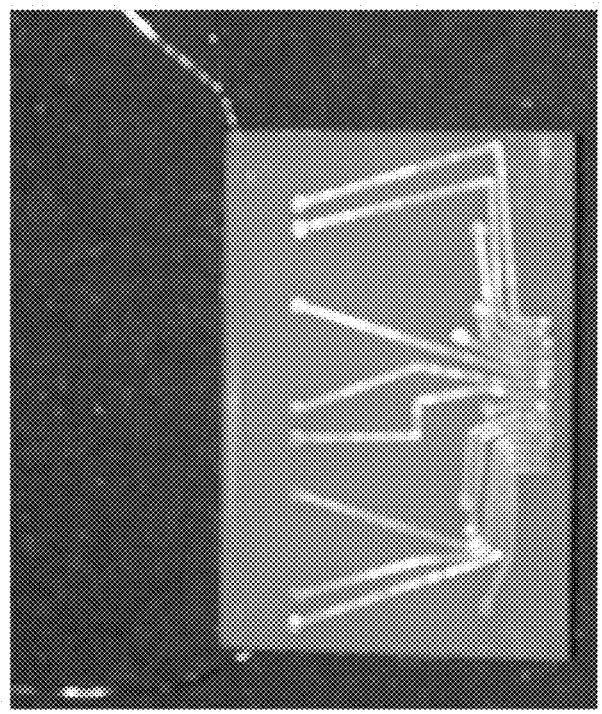
FIG. 7A is a schematic of an example of a resistor from the back side configured for use in an embodiment.

FIGS. 7A-7B illustrate an example of a type of resistor that may be used in the embodiments herein. In one embodiment, the resistor of FIGS. 7A-7B may be arranged in series of 10, 11, 12, 13, 14, 15, 16, 17, 18, 19 and 20 resistors in series. In another embodiment, the resistors in series are 10 kΩ resistors. As an example, as shown in Table 1, the resistors of FIGS. 7A and 7B arranged in series and in resultant resistance testing demonstrated the proper resistance when the sensor is moved back and forth across the range of the sensors movement.

TABLE 1

Resistor Values Across The Sensor

| Resistor # | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Value (kΩ) | 10 | 20 | 30 | 40 | 50 | 60 | 70 | 80 | 90 | 100 | 110 | 120 | 130 | 140 | 150 |

Alternatively or in addition to resistive elements, some embodiments include capacitive elements to measure strain in terms of capacitance. In embodiments, the resistive (or capacitive) elements are non-resonant or resonant. In embodiments incorporating resonant elements, the resistance (or capacitance) is read by RF-scanning for the resonant frequency. Further, some embodiments include a sensor comprising a compliant, elastomer-based strain gauge (for example comprising carbon nanotubes) configured to conform to ocular tissues and accurately measure the levels of strain expected therein. One example of such a sensor includes thin carbon-black-doped poly(dimethylsiloxane) for the strain gauge(s) and thick carbon-nanotube-doped PDMS for the interconnects. In some of these embodiments, the sensor 104 based on the carbon nanotubes is not configured similar to the sensor shown in FIG. 1B. Instead, the sensor 104 in FIG. 1A is a sheet of the carbon nanotube-doped PDMS or similar high yield material that provides electrical changes as function of mechanical stretch.

With reference now to FIG. 3A, a sensor 200 according to another embodiment is illustrated. The sensor 200 includes a fixed member 202 and a movable (relative to member 202) member 204. The fixed member 202 includes a first anchor member 206 and the movable member 204 includes a second anchor member 208. The anchor members 206, 208 are configured to be secured to discrete regions or points on or in the sclera, and to be freely movable with respect to one another as the sclera expands or contracts (the double arrow of FIG. 3A). In some embodiments, the anchor member 208 includes all or part of a lower surface of the movable member 204. An electrode 210 extends from the fixed member 202. The movable member 204 includes an array of conductors 212(*a*)-212(*f*) which are electrically isolated from one another and from any surrounding components by insulators 214(*a*)-214(*g*) and which are connected, respectively, to an array of resistors 216(*a*)-216(*f*). As the sclera expands, the second anchor member 208 moves away from the first anchor member 206 such that the electrode 210 closes the electrical circuit between a different set of conductors 212 and resistors 216 and therefore reflect a different level of resistance. In some embodiments, the sensor 200 and its components are encapsulated in any suitably elastic material, such as, for example, a silicone having a low Young's modulus. At a lower level of the sensor 200 (below the plane of the page, as illustrated in FIG. 3A), the anchor members 206 and 208 are fixed in a highly elastic material. At a middle level of the sensor (within the plane of the page, as illustrated in FIG. 3B), the anchor member 206 is fixed in a highly elastic material, while the electrode 210 and/or the movable member 204 is surrounded by a fluid or gel so as to allow free movement of the movable member 204 with respect to the electrode 210.

As shown in FIG. 3A, the anchor members 206 and 208 move with respect to one another as the sclera expands or contracts. The silicon bar on the left provide support for the electrode 210. In some embodiments, the support is needed because the electrode 210 is flexed prior to assembly into the sensor, thus causing it to press against the conductors 212, ensuring a proper electrical contact.

FIG. 3B shows a middle level of the sensor 200, with the resistors 216(*a*)-216(*f*) removed for clarity. An encapsulation material 218 is also shown. FIG. 3B illustrates that, at an IOP of 8 mm Hg, the displacement of the anchor members 206, 208 is L, and the measured resistance will reflect connection of the electrode 210 to conductor 212(*d*) (and, accordingly, resistor 216(*d*)). At a higher IOP of 30 mm Hg, the displacement of the anchor members 206, 208 is L+2(Δx), and the measured resistance reflects connection of the electrode 210 to conductor 212(*b*) (and, accordingly, resistor 216(*b*)). It should be noted that in this embodiment, the resistor 210 does not change its shape during the movement. Simply, the resistor 210 moves from a first position to a second position, thereby causing a difference in the connectivity to a conductor 212.

FIG. 3C shows a sensor 240 according to another embodiment. The sensor 240 includes a fixed member 242 and a movable member 244. The fixed member 242 includes a first anchor member 246 and the movable member 244 includes a second anchor member 248. An electrode 250 extends from the fixed member 242. The movable member 244 includes an array of conductors 252(a)-252(e), which are electrically isolated from one another and from any surrounding components by insulators 254(a)-254(f), and which are connected, respectively, to an array of resistors 256(a)-256(f). In some embodiments, the resistors 256(a)-256(f) are, tbr example, off-the-shelf size 01005 resistors available from Topline Corporation, or ROHM 03015 chip resistor, which is 0.3 mm by 0.15 mm by 0.10 mm. As the sclera expands, the second anchor member 248 moves away from the first anchor member 246 such that the electrode 250 closes the electrical circuit between a different set of conductors 252 and resistors 256. In some embodiments, the sensor 240 and its components are encapsulated in any suitably elastic material, such as, for example, a silicone having a low Young's modulus. At a lower level of the sensor 240 (below the plane of the page, as illustrated in FIG. 3C), the anchor members 246 and 248 are fixed in a highly elastic material. At a middle level of the sensor (within the plane of the page, as illustrated in FIG. 3C), the anchor member 246 is fixed in a highly elastic material, while the electrode 250 and/or the movable member 244 is surrounded by a fluid or gel so as to allow free movement of the movable member 244 with respect to the electrode 250.

Figure 3D:
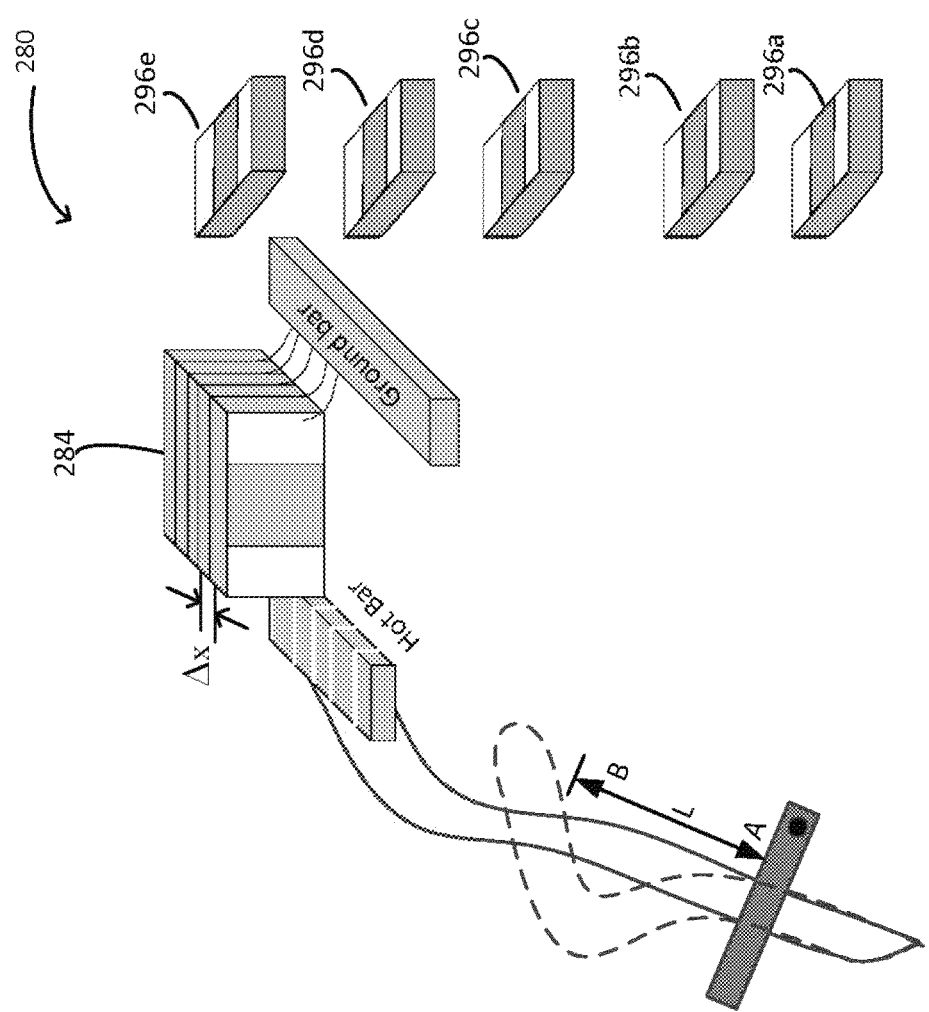
FIG. 3D is a schematic drawing showing a top view of an example of a sensor configured in accordance with yet a further embodiment.

FIG. 3D shows a sensor 280 according to yet another embodiment. The sensor 280 can have a similar configuration to the sensors 200, 240 described above, except that the movable member 284 can include a stack of resistors 296(a)-296(d) such as, for example, size 01005 resistors available from Topline Corporation of or ROHM 03015 chip resistor, which is 0.3 mm by 0.15 mm by 0.10 mm. Thus, in embodiments, the resistors are internal or external to the movable member. That is, in some embodiment, the resistors form part of the movable member, while in other embodiments, the resistors are physically separate from (and merely electrically connected to) the movable member within the sensor.

Another embodiment includes a conductive wire-in-tube sensor configuration, in which the sensor comprises a wire coated in an insulating, compliant material and having exposed tips. At one end of the sensor (i.e., a first anchor member), the outer tube (or other insulating layer) is glued, sutured, or otherwise attached to a point on the sclera. At the other end of the sensor (i.e., a second anchor member), the exposed end of the wire is glued, sutured, or otherwise attached (e.g. barbed and engaged with the tissue) to a separate point on the sclera. As the sclera expands or contracts, the wire stretches and its resistance changes due to the elongated electrical path. In some embodiments, the wire comprises any suitable conductive material such as, for example, gold. Such an embodiment is configured without encapsulation if desired.

In some embodiments, the encapsulated wire makes of a loop of an antenna on the implant. In these embodiments, the change in the electrical path length is detectable by the external reader. For example, the external reader provides an RF signal that creates an electrical current on the implant antenna that energizes the implant electronics. The implant electronics then produce an RF signal that varies with the strain on the sensor. This RF signal is then read by the external reader. In some embodiments, the implant electronics providing this utility is a transponder chip such as those commonly used in RFID tagging. In other embodiments, the implant electronics includes a SAW (Surface Acoustic Wave) system design.

Figure 4:
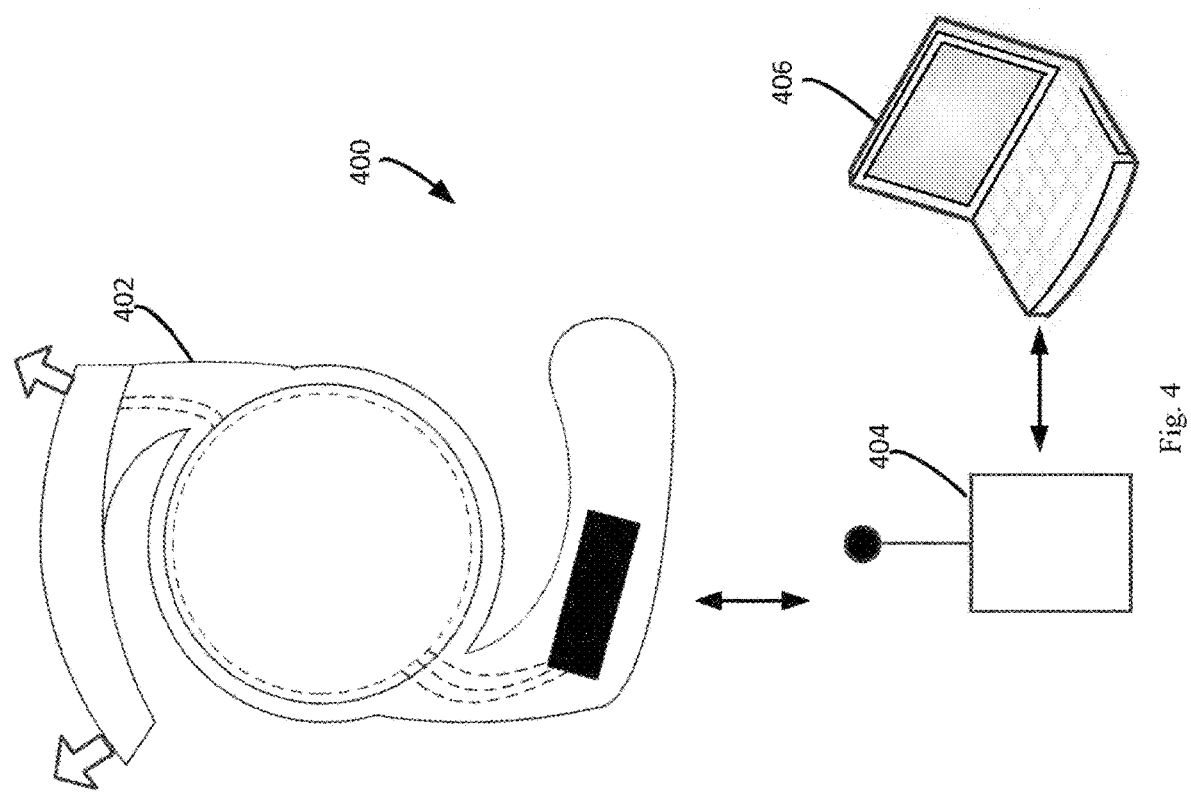
FIG. 4 is a schematic drawing showing an example of a system for monitoring eye health, configured in accordance with an embodiment.

With reference now to FIG. 4, a simplified block diagram of a system 400 for monitoring eye health in accordance with an embodiment is shown. The system 400 includes an implant 402 configured to be implanted in a patient's eye and to measure scleral strain, and an external reader 404 which is optionally worn by the patient (e.g., in or on a pair of glasses) or is optionally held by the patient or a healthcare practitioner. The implant 402 optionally includes a strain sensor and a telemetry system (including, for example, a transponder and an antenna) for transmitting data (e.g. electrical measurements, strain readings, and/or IOP calculations) to the external reader 404. In some embodiments, however, the antenna is disposed in or on the reader instead of in or on the implant. Communication and/or powering of the sensor are optionally performed wirelessly between the telemetry system and the reader. In some embodiments, however, the implant includes a battery so that external powering is not required. In some embodiments, the reader includes storage and a display to record and display the data received from the implant 402. In some embodiments, the reader is configured to convert a measured level of resistance to a corresponding level of scleral strain. In some embodiments, the reader is also configured to convert a measured level of resistance to a corresponding level of IOP, based at least in part on one or more reference levels of IOP recorded intraoperatively. In some embodiments, the conversion is performed by a processor in the implant and simply transmitted (as strain or level of IOP) to the reader.

In some embodiments, the reader is a wireless reader that communicates with the sensor using RF technology (e.g., through interrogation/response or frequency scanning).

In other embodiments, the reader is a camera that uses visual or thermal imaging to read the strain measurements from the sensor. In the case of thermal imaging, in some embodiments, at least two spike-type members are inserted into ocular tissue at some relatively close but measurable separation distance. As the sclera expands due to increased pressure, the two spikes separate. By intentionally selecting a spike material that has a thermal emissivity notably different from the nearby ocular tissue, the thermal spacing is externally monitored wirelessly using thermography. In these embodiments, a 2D thermal imaging hardware installed on the external unit (for example, a pair of eyeglass frames) records multiple digital thermographs of the implant location and, using post processing techniques such as averaging the images across time, an accurate measurement of the spikes separate is realized. For improved signal, the spike can be kept close to the ocular surface since it is known that the water in the ocular tissues will tend to absorb the infrared radiation. In these and other embodiments, the reader is configured to communicate (wirelessly if desired) with a mobile device 406 such as a laptop or Smartphone.

In one embodiment, a healthcare practitioner injects a dye into the ocular tissues to increase the contrast between the anchor members and the surrounding tissue, allowing the camera to visually detect the displacement (or an increase in displacement) between the anchor members. This is can be done in a manner similar to that explained above for thermography.

In embodiments such that the reader is a wireless reader that communicates with the sensor using RF technology, the external reader optionally provides an RF signal that creates an electrical current on the implant antenna that energizes the implant electronics. The implant electronics then produces an RF signal that varies with the strain on the sensor and is read by the external reader. In some cases, the implant electronics is a transponder chip, such as those commonly used in RFID tagging. In other embodiments, the implant electronics includes a SAW (Surface Acoustic Wave) system design.

Figure 5:
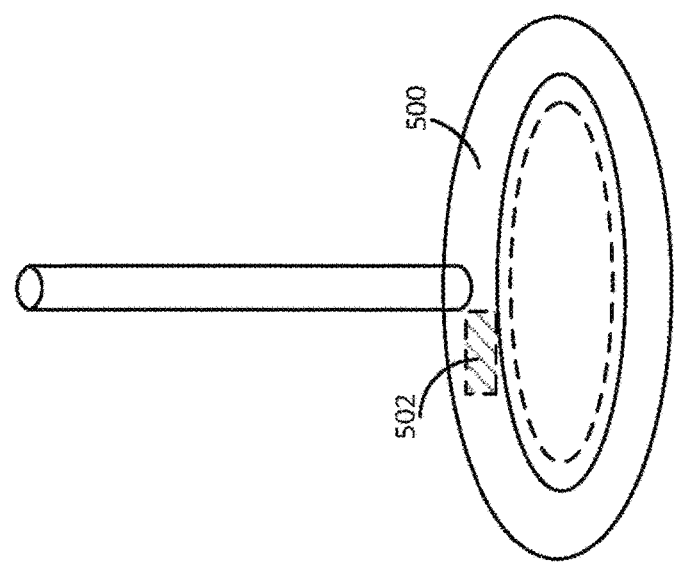
FIG. 5 is a front view of an implant including a sensor according to another embodiment.

As described above, in some embodiments, the implant 100 optionally comprises an intraocular lens (IOL) having a strain sensor 104 disposed on or in the lens or extending from the lens. In other embodiments, the implant 100 optionally comprises an intraocular lens (IOL), either phakic or pseudophakic, having a strain sensor 104 disposed on or in the lens or extending from the lens. In still other embodiments, for example as illustrated in FIG. 5, the implant 100 optionally comprises a plate 500 configured to be implanted under the conjunctiva, with a strain sensor 502 disposed on or in the plate or extending from the plate. In a plate configuration, a sensor optionally has at least two anchor members disposed, respectively, at spaced-apart locations on or in the plate such that they are secured to respective locations on or in the sclera. The sensor optionally includes a highly elastic material (for example having a Young's Modulus equal to or lower than that of the ocular tissue(s) to which the anchor members are secured) such that the anchor members are freely movable with respect to one another as the sclera (or other ocular tissue to which they are anchored) expands and contracts. In an embodiment incorporating a plate, the plate is optionally formed from a material having a low modulus of elasticity such as, for example, a silicone. In some embodiments, the implant includes an Ahmed valve (available from New World Medical Rancho Cucamonga, Calif.), and having a drainage tube. In such an embodiment, the anchor members are secured to the sclera, either under a tube that has previously been implanted or during trabecular surgery. In some embodiments, the attachment area is the pars plana. Attachment mechanisms can be small spike members, such as those shown in IOL versions, ophthalmic glue, such as a fibrin glue, or sutures.

In some embodiments, the implants 100 disclosed herein are implanted in other locations in the eye. For example, in an embodiment comprising an IOL or a PIOL, the anchor members are secured to the ciliary body or at the pars plana from underneath the sclera. During implantation, the surgeon can direct the haptic on which the sensor is disposed to the correct orientation for anchoring of the anchor members.

Once the implant is in place and the anchor members are secured to the ocular tissues, the intraocular pressure can be intraoperatively manipulated to establish one or more baseline or reference values of scleral strain and, if desired, to calibrate the sensor for IOP measurements. For example, IOP can be intraoperatively lowered down to a baseline level (such as, for example, 10 mm Hg), and a baseline level of scleral strain can be recorded at that pressure based on the electrical response (e.g. the measured resistance) of the sensor. The IOP can then be increased to higher levels (such as, for example, up to 30 mm Hg specific increments, such as 2 mmHg or 5 mmHg), and a reference level of scleral strain can be recorded at those higher pressures based on the electrical response (e.g. the measured resistance) of the sensor. These parameters are then used post-operatively to estimate IOP based on measured levels of resistance and/or strain.

Figure 6:
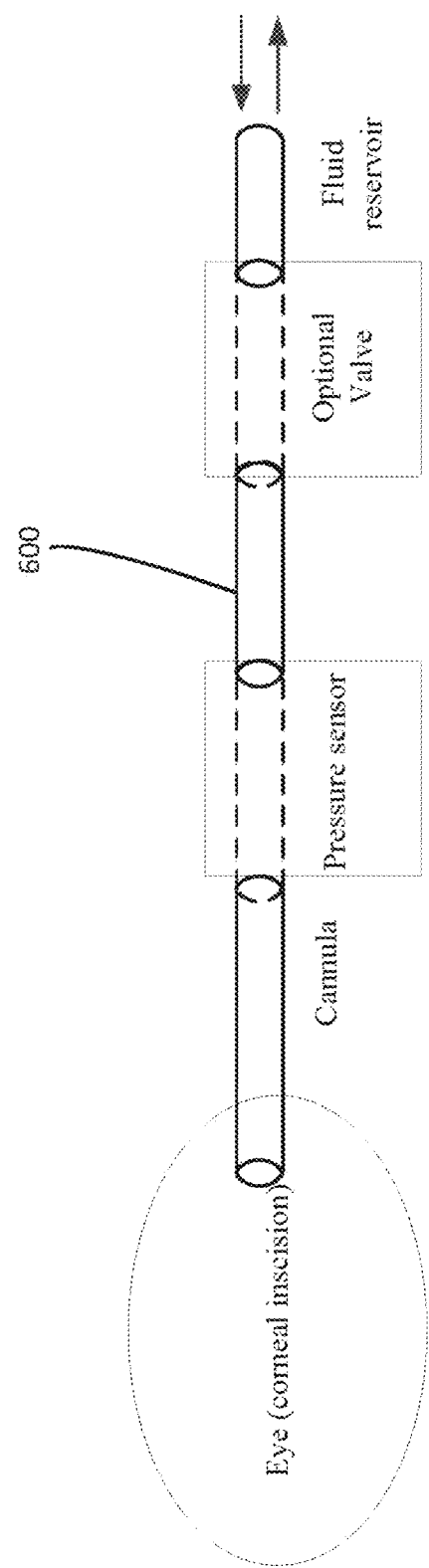
FIG. 6 is a schematic drawing of an apparatus for intra-operatively controlling eye pressure, suitable for use with an embodiment.

FIG. 6 is a schematic drawing of an apparatus 600 for intraoperatively manipulating eye pressure, suitable for use with an embodiment. In some embodiments, the baseline pressure (e.g., 10 mmHg) also serves as a consistent baseline for the strain measurement, thus providing patient-to-patient comparisons. For example, one can record a patient's strain as "+1%", which implies 1% increase from the 10 mmHg baseline. In other words, the notation "+1%" indicates the pressure rise in the eye has caused the two anchors of the sensor to move a distance of 1% apart from that recorded when the patient's pressure was 10 mmHg during surgery (e.g., 10.0 mm @ 10 mmHg became 10.1 mm at, say, 15 mmHg).

In another aspect, disclosed herein are methods of monitoring eye health in a patient using the implant 100. The method comprises the steps of obtaining an output of electrical resistance from an implanted device in the eye of an individual, as described herein, comparing the resistance output to a baseline value, and correlating the change in the electrical resistance to a disease state in the individual.

In some embodiments, the baseline value is obtained immediately after the device is implanted. In other embodiments, the baseline value is obtained several days after the implantation, to allow for any potential inflammation of the sclera and other tissue to be resolved. In some embodiments, the change in electrical greater than a certain value, for example 1, 10, 30, 50, 100, etc., ohms indicates the onset of glaucoma. In other embodiments, the change in electrical resistance is expressed in terms of the distance between the anchor members, as discussed above. In other embodiments, the change in electrical resistance is expressed in terms of a percent increase in the sclera strain, as discussed above.

Sensor Based System for Monitoring Structural Fatigue:

While the embodiments shown in FIGS. 1B, 1C, 2A-2D, and 3A-3D have been previously shown to be used within surgically implanted devices to monitor scleral strain in an eye, the same concepts can be utilized in other applications, such as attaching to a user's skin for biomechanical monitoring. Additionally, the same concepts can be utilized in a larger-scale fashion to monitor strain on any item capable of undergoing stress-related deformation, e.g., buildings, bridges, and other structures.

In this larger-scale embodiment, there is envisioned a system for monitoring strain on a structural surface to which the system is attached having at least first and second anchor spaced-apart members. The first and second anchor members are configured to be secured to respective first and second anchor locations on or in the surface to be monitored. Further, the first and second anchor members are movable with respect to one another.

The system further includes a sensor having a plurality of resistive elements. The sensor is configured to measure electrical resistance between two electrical conductors and to generate a signal representing said electrical resistance. The sensor measures structural strain based at least in part on a displacement between the first and second anchor members.

The system further includes a transmitter configured to transmit the signal and an external reader configured to receive information transmitted by the transmitter.

In certain embodiments of this system, the first anchor may be connected to a resistor housing and the second anchor member may be connected to a component housing. Additionally, or alternatively, the sensor may include a plurality of resistive elements, which may be connected in parallel and/or each have a different resistance.

Imaging Based System for Monitoring Eye Health:

In another embodiment, disclosed herein is a system for monitoring eye health, the system comprising: a scleral strain monitor comprising
- a) a wearable pair of eyeglasses comprising
  - i. one or more image sensors,
  - ii. a CPU,
  - iii. a memory storage device,
  - iv. one or more connecting wires, and
  - v. and a power source; and
- b) at least one preselected target region on or in the sclera, wherein the CPU receives images from the image sensors and then transmits the images to the memory storage device.

In another embodiment, disclosed herein is a method of monitoring eye health, the method comprising: providing a scleral strain monitor comprising
- a) a wearable pair of eyeglasses comprising
  - i. one or more image sensors,
  - ii. a CPU,
  - iii. a memory storage device,
  - iv. one or more connecting wires,
  - v. and a power source; and
- b) at least one preselected target region on or in the sclera, wherein the CPU receives images from the image sensors and then transmits the images to the memory storage device.

In general, the imaging based systems and methods disclosed specifically pertain to the early detection and diagnosis of glaucoma. The imaging apparatus of the disclosed systems and methods is designed as a wearable pair of eyeglasses capable of viewing the eye and collecting data in the form of images that will aid in the early detection of glaucoma symptoms.

In order to determine scleral strain, it is necessary to sense small displacements of separated points on the sclera. This can be done in a non-contact scenario, through direct imaging of the surface of the eye, if we can either establish image-to-image correspondence of different points on the eye or measure overall characteristics related to scleral size. We disclose several methods for accomplishing this task, without excluding others that may be obvious extensions or modifications.
1. Measurement of distance between two symmetric objects implanted in or placed on the eye.
2. Measurement of distance between two asymmetric objects implanted in or placed on the eye.
3. Measurement of distance between two previously characterized "target regions" on the eye.
4. Measurement of the spatial frequency characteristics of one or more regions of the eye, to establish spatial scale.

Figure 10:
FIG. 10 is a view of a measurement between two symmetric objects.

Measurement Between Two Symmetric Objects:

Scleral strain is the ratio of the change in a distance to the original magnitude of the same distance at rest or at a reference stress level. Given two objects on the sclera, repeated measurements of the distance between the objects will give a history of the strain. If one or more readings can be performed at a known level of strain or intraocular pressure, we can use simple spherical trigonometry to calculate the strain for any image taken that contains both objects. To increase the accuracy, we propose the use of geometrically regular objects (such as circles) for which the centroid can be measured accurately. Accuracy on determining object centroids can be much less than one pixel. Refer to FIG. 10 for one possible scenario.

Utilizing a suitable image capture system, images of the sclera of the eye are acquired and processed to determine the positions of two fixed targets implanted into or placed onto the eye. In some embodiments, the two separated symmetric implanted objects are spike-type members and fabricated from surgical steel or Teflon. In some embodiments, the two separated symmetric objects may comprise two dots or the two separated asymmetric objects comprise a dot and an arc. In some embodiments, the two separated symmetric objects may comprise markers, the markers comprising ink or dye. These targets are biologically inert and inelastic, so that the distance between their centroids is an accurate indication of the perimeter of the eye, and thus is proportional to the scleral strain. The image is enhanced and dimensions are extracted. For this method, spatial calibration is important and is not delivered directly by the method, as the target objects are likely to be too small to allow their size to indicate spatial resolution sufficiently accurately. There are at least two ways to calibrate the images taken: by measuring the radius of the iris or by measuring the displacement of a light point source impinging on the eye from a known angle to the imaging plane. This "triangulation" method will result in the x-y position of the point being proportional to the distance from the light source to the eye.

Figure 11:
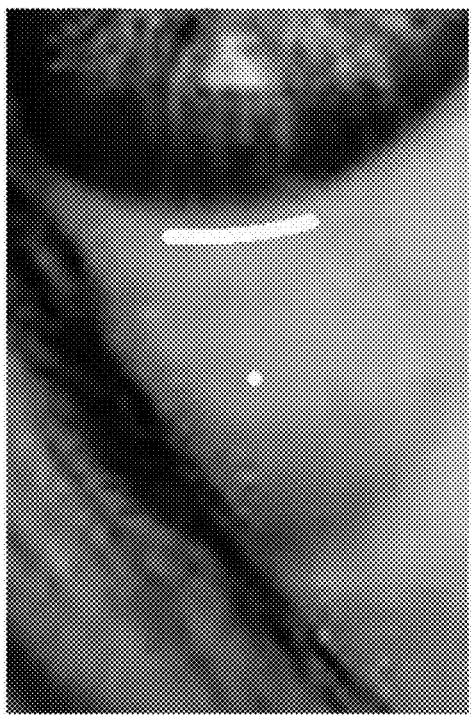
FIG. 11 is a view of a measurement between two asymmetric objects.

Measurement Between Two Asymmetric Objects:

In an actual scenario, it may be that the distance from the image collection apparatus to the eye surface varies. Without some correction, this difference in distance could be misinterpreted as a change in the scleral strain. To allow dynamic correction of the working distance, one of the targets can be designed to give an independent measurement of the spatial calibration (in pixels per millimeter, for example). Referring to FIG. 11, which shows one possible configuration, the large arc object has a known radius of curvature that will not change, because of the inelastic nature of the object. In some embodiments, the two separated asymmetric implanted objects are spike-type members and fabricated from surgical steel or Teflon. In some embodiments, the two separated asymmetric objects may comprise two dots or the two separated asymmetric objects comprise a dot and an arc. In some embodiments, the two separated asymmetric objects may comprise markers, the markers comprising ink or dye. This can be used to establish the spatial calibration of the entire scene. Then, measurement of the offset between the two objects can be interpreted as a spatial distance and insensitivity to change in working distance is achieved.

Figure 12:
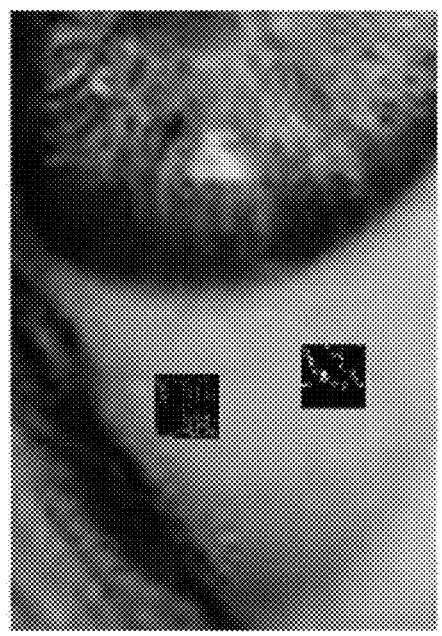
FIG. 12 is a view of a measurement between two target regions.

Measurement Between Two Target Regions:

It may be that the need to implant target objects in the eye is objectionable or prohibitive in some cases. However, the surface of the sclera has distinct texture due to the patterns of blood vessels and other tissues. By selecting two suitable regions of the sclera some known distance apart and storing a processed "template" for these areas, standard target locating techniques (such as normalized grayscale correlation) can be used to accurately locate the target regions in any image of the eye. The measured distance is then an indication of the difference in strain from the time at which the target templates were stored. We propose storing several target images (three, for example) and measuring the inter-target distances to provide redundant measure of the strain. As above, spatial calibration, if desired, can be achieved by either measurement of the radius of the iris, or by a light triangulation method. Reliable templates may be collected using gray-scale enhancements or an edge operator. FIG. 12 shows the concept of collection of the template images. One method of extracting reliable targets from a natural image of the eye is shown here; deriving normalized edge images of areas of the sclera with suitable natural texture. In some embodiments, at least one preselected target region are two distinct sclera regions. In some embodiments, the two distinct sclera regions are areas of the sclera with distinct textures and with a measurable distance apart. Within two or more subregions of interest, possibly defined at physiologic calibration time, the edge image is extracted using a standard edge detection method such as difference of Gaussians. These edge images are the templates which will be located in subsequent images using a technique such as normalized gray-scale correlation. The relative shift of the located positions is used to compute the scleral strain.

Figure 13:
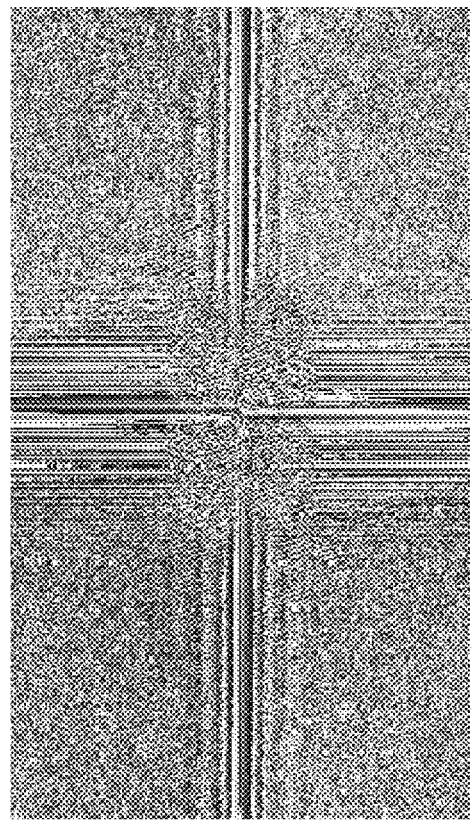
FIG. 13 is a view of a measurement of spatial frequency characteristics.

Measurement of Spatial Frequency Characteristics:

All images with nontrivial content have a spatial frequency "spectrum", the relation between spatial frequency and ratio of content in the image. Changes in size of an elastic object in the image result in a "shift" of its spectrum to higher or lower spatial frequencies. Thus, it is possible to find the highest correlation between the trained and sampled frequency spectra, and to interpret the shift as a measure of the expansion or contraction of the image. In some embodiments, the preselected target region is a frequency spectrum of one or more regions of the eye or the complete surface of the eye. This approach has the advantage of being global, rather than limited to a certain region of interest, and therefore has the potential to be less sensitive to local artifacts or anomalies. As above, spatial calibration can be achieved by either measurement of the radius of the iris, or by a light triangulation method. FIG. 13 shows the spatial frequencies of an image of an eye.

Figure 14:
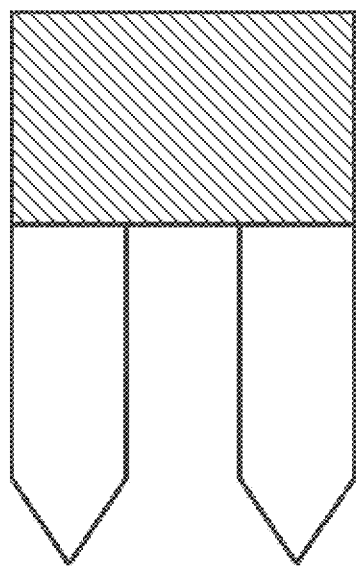
FIG. 14 is a view of a marking tool.

Targets:

The targets mentioned above may be implanted devices fabricated from a biologically inert material such as surgical steel or Teflon. This allows for geometrically precise manufacture. Alternatively, the targets may be markers placed onto the surface of the eye, composed of a safe ink or dye product. In some embodiments, the markers may be near-IR ink, such as a fluorescent ink. In another embodiment, the markers may be a gentle laser mark. This approach provides a less-invasive marking process. One possible approach is to use a marking tool designed to easily create two "dots" with the proper nominal distance between them. Marking could then be done in an in-office procedure, using such a tool. The concept for this tool is shown in FIG. 14. In some embodiments, the disclosed systems and method comprise using a dual marking tool for applying the markers to the surface of an eye as two markers that are separated by a fixed distance predetermined with the dual marking tool. In some embodiments, the targets or markers are imaged by the one or more cameras from 2 mm, 3 mm, 4 mm, 5 mm or 6 mm distance from the limbus or edge of the iris.

Customization:

Due to variations in physiology, it may be advisable to customize the algorithmic approach to each individual user. This can be imagined as an in-office visit during which a number of image sets are collected. A trained operator will examine each image set and process them in a number of ways, selecting the processing steps that will give the most accurate performance. Parameters that may be selected in this process include: preprocessing and enhancement, regions of interest, target sizes and geometries.

Metrics:

The first metric to be extracted, scleral strain, is expected to have the most direct relationship with IOP and the effects of glaucoma. However, several other metrics will be extracted and continuously tracked. These may include strain in both axial and tangential directions, the ratio of change in strain to strain, and geometric properties of the eye, such as iris diameter and corneal curvature. Studies suggest that the sclera is more rigid with advanced age, so the mapping from strain to intraocular pressure may change over time for a given user, and other metrics may be used to detect onset of glaucoma. In some embodiments, the ratios of ocular pulse amplitude and IOP are an additional metric of the disclosed image based systems and methods.

Apparatus:

FIG. 9 illustrates an example of a scleral strain monitor comprising a wearable pair of eyeglasses 900 comprising one or more image sensors with micromotors 904, a CPU and a memory storage device 901, connecting wires 902 and a power source 903. To support the image-based strain measurement method, we propose a wearable apparatus such as a pair of glasses.

In some embodiments, the disclosed image based systems and methods may comprise the use of a camera with the following specifications:

Type: Mini;
High Definition Support: 1080P (Full-HD);
Memory Card Type: Micro-SD/TF;
Sensor Technology: CMOS;
Video Format: AVI;
Resolution: 1920*1080, 30 fps/1280*720/640*480;
Lens Specs: 5 Mege pixels CMOS camera;
Video coding: M-JPEG; and
Power Adaptor: 5V DC/500 mAH.

Figure 9A:
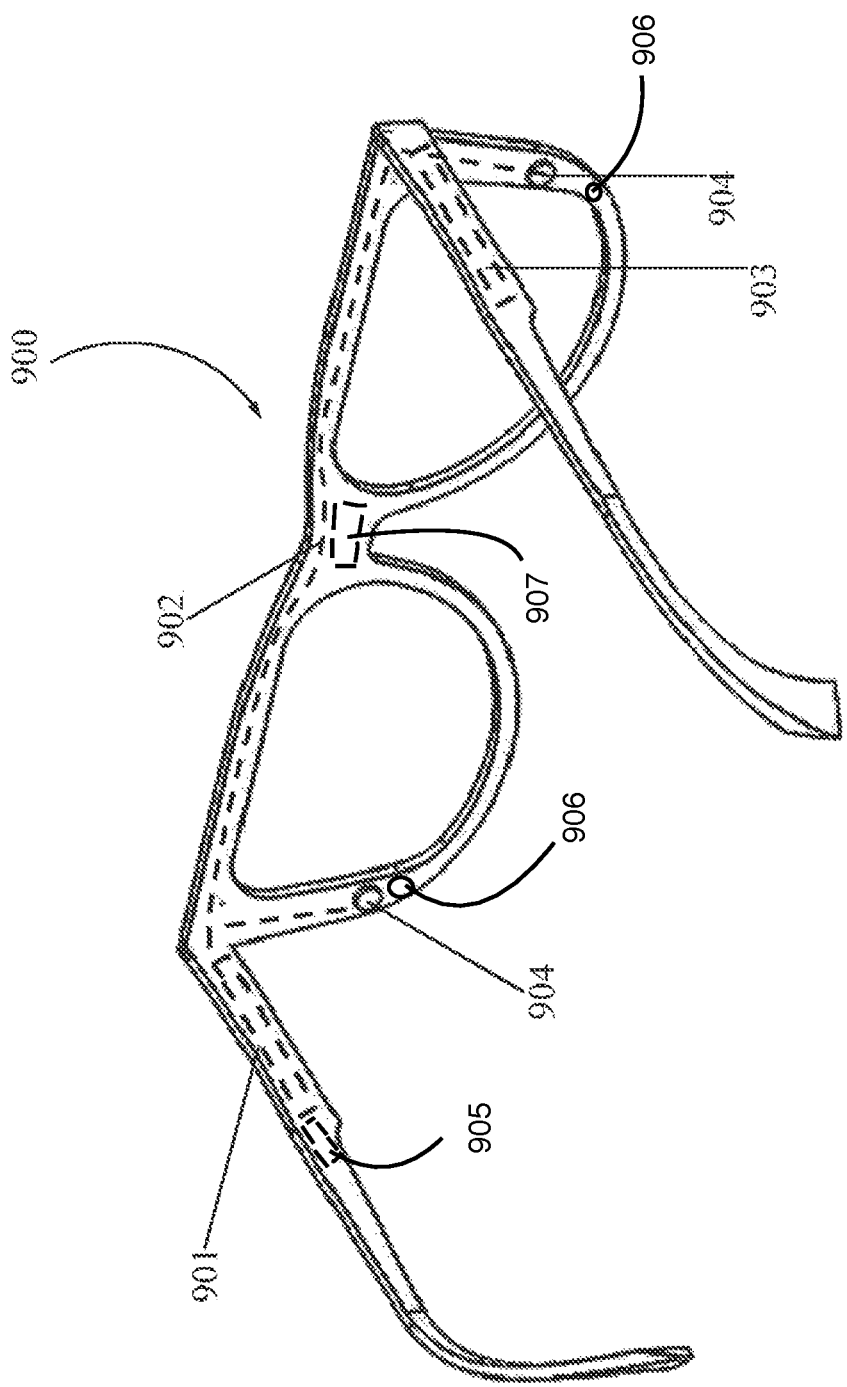
FIG. 9A is a view of an example of a scleral strain monitor comprising a wearable pair of eyeglasses configured with image sensors, a CPU, a memory storage device, connecting wires, and a power source, wherein the image sensors are located on the outside frame of the eyeglasses.
Figure 9B:
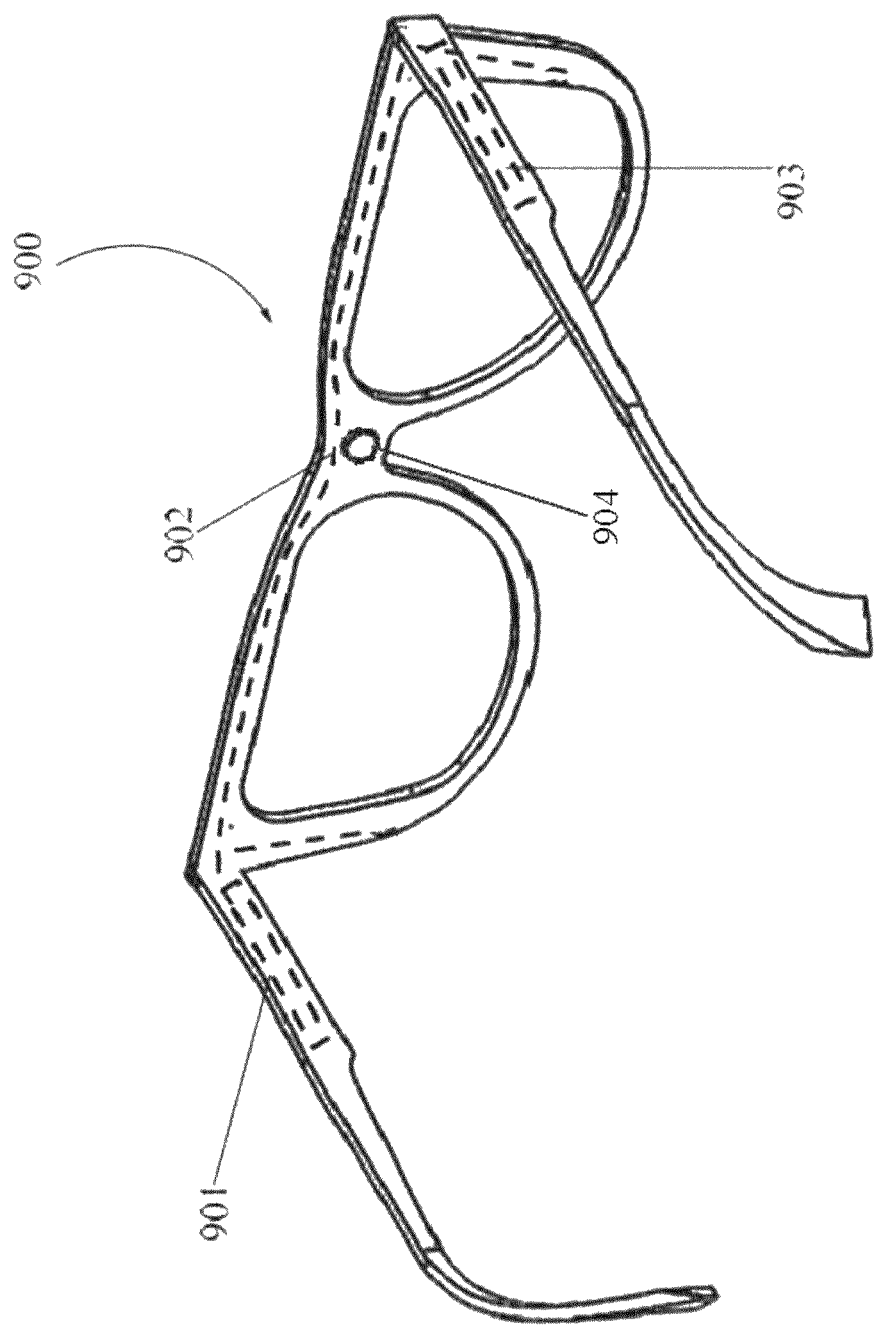
FIG. 9B is a view of an example of a scleral strain monitor comprising a wearable pair of eyeglasses configured with image sensors, a CPU, a memory storage device, connecting wires, and a power source, wherein the image sensors are located on the inside nose portion of the eyeglasses.

The lenses may be plain or prescription as needed. In the frame, a pair of small digital sensors with optical elements is positioned to capture images of each eye. The sensors may be facing toward the eyes, or the optical path may be folded. As shown in FIG. 9, the image sensors may be mounted inside the eyes, in the nosepiece of the glasses, or in the frames to the side of the head. For example, in some embodiments shown in FIG. 9A the image sensors are one or more cameras embedded in the frames of the wearable pair of eyeglasses 900, and located near the outer portion of frames on both sides. The cameras are oriented with the lenses facing the sclera and looking at an outer eye sclera using HD video capturing at about 30-60 frames per second. In another embodiment shown in FIG. 9B, the one or more cameras are located near the nose of the frames and with lenses oriented to image the inner eye sclera.

In some embodiments, the one or more cameras may comprise one or more Macro lenses in front of the camera to allow for the short focusing distance between the eye glass frames and the eye being examined. In some embodiments, a double macro lens may be employed.

In some embodiments, the disclosed system includes a design including two mirrors near the nose of the frames of the eye glasses aligned at about 45 degrees relative to each other, such that light of sclera is reflected off one mirror to the other and then into a camera in the nose of the eye glass frames. The design affords the advantage of folding the light path, which allows for a potentially longer light path and allowing for increased lens power.

A digital signal processor or other CPU extracts the relevant measurements proportional to strain from each pair of images, and either stores the images and data to a Micro-SIM or other memory card, or transmits it to a host (Smartphone, wearable computer or nearby computer) using an RF connection 905. In some embodiments, the images are transmitted with wireless streaming from frames to a Smartphone or other nearby device with computing and internet capabilities.

In some embodiments, the disclosed systems and methods utilize a wearable pair of eyeglasses calibrated to take measurements of markers in and on the eye to determine if pressure in the eye has increased by measuring sclera stretch and storing the images on an onboard Micro-SIM card. In some embodiments, the disclosed systems and methods utilize a wearable pair of eyeglasses that will store significant sclera measurements on an onboard Micro-SIM card in order to conserve storage space with non-significant images. In some embodiments, the disclosed systems and methods utilize a wearable pair of eyeglasses capable of transferring the data stored on the Micro-SIM card wirelessly (e.g., Bluetooth) to a computer or other device for viewing purposes.

Testing will determine the ideal interval for image collection and processing. It is anticipated that the data collection interval will be dynamic; for example, a rise in pressure might trigger more frequent data collection. This aperiodic collection of data may be based on previous data collected and allow for reduced collection of data to extend battery life of the system.

Imaging Spectrum:

It will be advantageous to control the illumination for acquiring the eye images. In some embodiments, the wearable pair of eyeglasses further comprises one or more illumination sources 906 capable of controlling the illumination levels of an eye of a wearer. Various illumination approaches may be used to provide illumination of the eye under examination (i.e., Red, Infrared, LED's, etc.), in some embodiments, one or more illumination sources 906 is capable of emitting light at 800 nm. However, it is undesirable to shine a light, either continuous or pulsed, at the eye; this could cause distractions and would certainly be annoying. We propose to use a illumination source 906 that is non-distracting. One way to do this is to illuminate in the near-infrared part of the EM spectrum, nominally at 800 nm. Light in this range is essentially invisible to the human eye, but most CMOS imagers can readily capture the light in this range. Other options for eliminating or reducing the annoyance of the illuminator exist and may be part of relevant systems.

In some embodiments, the software that tracks and categorizes the conjunctiva (darker) veins verses the sclera (fainter) veins either by relative image intensity or recognizing which veins move relative to other veins as patient moves eye.

Spatial Calibration:

As mentioned above, the measured displacement must be well-calibrated to be compared to the baseline measurement, for calculation of strain. The nature of a wearable device such as glasses makes it difficult to guarantee that the optical working distance will remain constant; one solution is to calculate the spatial resolution in the imaging plane from the image itself, thereby provide a correlation between pixels and an absolute spatial value, such as millimeters. Among the methods to do this are: selection of a target that contains precise dimensional information independent of strain, such as a portion of an arc with known radius; measurement and computation of the radius of the iris; and light triangulation to measure the working distance itself.

In some embodiments, the system needs only to monitor the change in displacement relative to initial displacement in an accurate manner and may not need to provide a conversion from pixels to an absolute spatial value, such as millimeters. However, the depth of field may cause artificial signal (i.e, measurement noise) since objects in the back of the depth of field appears to grow by about 10% when moving to the front edge of the depth of field. In some embodiments, the mechanical mounting of the lens in front of the imaging sensor translates such that the distance between the lens and sensor can be easily controlled via a micrometer in a fashion very similar to autofocus systems common on current camera systems. In another embodiment, the lens begins at one extreme position, causing images to be out of focus, and then moves such that images become in focus and continues to translate until the other extreme position is obtained and images are again out of focus. In some embodiments, approximately 50-100 images are captured during this process with both early images and late images being out of focus. Each image to be used for strain analysis can then be, for example, the first image in which the marker (veins) of interest becomes in focus as one moves frame-by-frame through the video starting with the camera too far away for the maker to be in focus. These positions are termed "just-in-focus-small" where the "small" distinguishes the images from the just-in-focus-large images, which would be observed if the camera were too close to be in focus and slowly moving further back until the marker was in focus. In the latter, the marker would appear approximately 10% larger than in the just-in-focus-small images. Similarly, the just-in-focus large images could be used for analysis.

Physiologic Calibration:

The method further comprises establishing a physiologic calibration of the scleral strain, the physiologic calibration comprising a) tilting a wearer in a reclining chair or a reclining bench from an upright position to a backwards supine position and a range of selected angles between the positions;

b) collecting an intraocular measurement from the wearer with a tonometer at each of the selected angles;

c) collecting a scleral strain measurement with the reader at each of the selected angles and converting the scleral strain measurements to the corresponding calculated interocular measurements;

d) comparing the interocular measurements of Step b) with the calculated interocular measurements of Step c); and e) adjusting the reader to align the scleral strain measurements and repeat to confirm that the reader is calibrated against the interocular measurements of Step b).

In some embodiments, an accelerometer 907 is integrated into the eye glasses and communicates with the onboard CPU. The accelerometer 907 is used by system such the software can take into account if IOP (Strain) increases simply due to body position (when patient is not in physiological calibration) and can also provide an accurate means of measuring the angle of the reclining in step (c) during the wearer's physiological calibration. On board hardware could include temperature and/or pressure sensors as well, to further explain changes in sclera strain, as IOP changes can be induced by environmental changes such as a lower-pressure airplane cabin.

The method further comprises establishing a physiologic calibration of the scleral strain, the physiologic calibration comprising administering glaucoma medication at a does suitable for lowering an intraocular pressure of the eye.

Use as a reliable glaucoma monitoring tool requires that the wearable apparatus and software be calibrated to the wearer. This may be done as part of an in-office visit. In one possible approach, the wearable apparatus is used to conduct measurements from the eyes, while a standard intraocular pressure measurement system is used. The combination of these two readings establishes the correspondence. This process is repeated while the wearer is in the normal posture, and while they are tilted backwards over a range of angles. Because this tilting will naturally increase the IOP, the resulting data produces a graph of the measured transfer function, allowing subsequent mapping back from a measured scleral strain to an intraocular pressure. In the disclosed methods, the recliner may be a reclining chair (i.e., ophthalmic examination chair) or a reclining bench.

Tablet Based Imaging System for Monitoring Eye Health

The imaging based system for monitoring eye health described above is envisioned to be utilized in an ongoing system wherein the patient wears the glasses containing the system the majority of the time. Additionally, or alternatively, similar noncontact imaging concepts may be utilized on a more infrequent basis performed by a healthcare provider.

Figure 15:
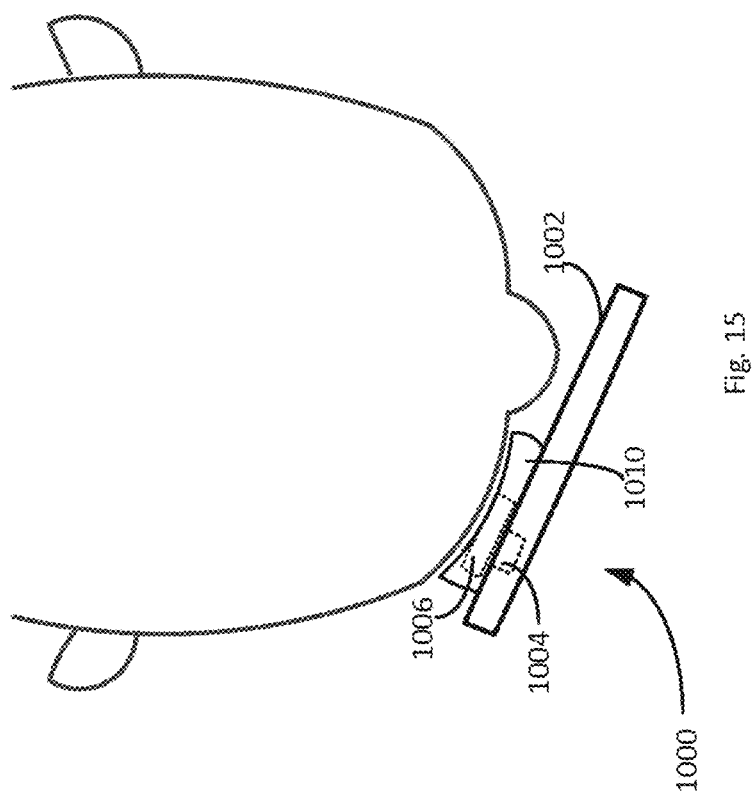
FIG. 15 is a top view of an example of a scleral strain monitor system comprising a lens assembly and comfort pad attached to a portable tablet device having a camera.
Figure 16:
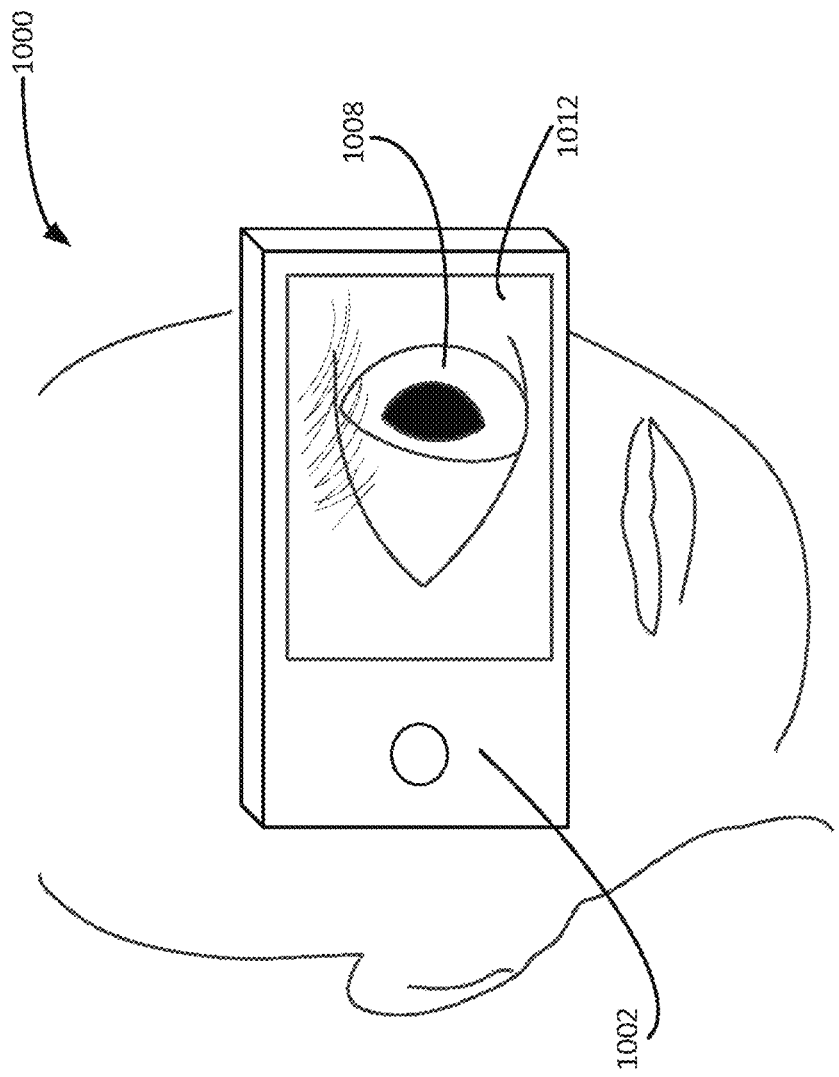
FIG. 16 is a front view of the scleral strain monitoring system of FIG. 15 in use.
Figure 17:
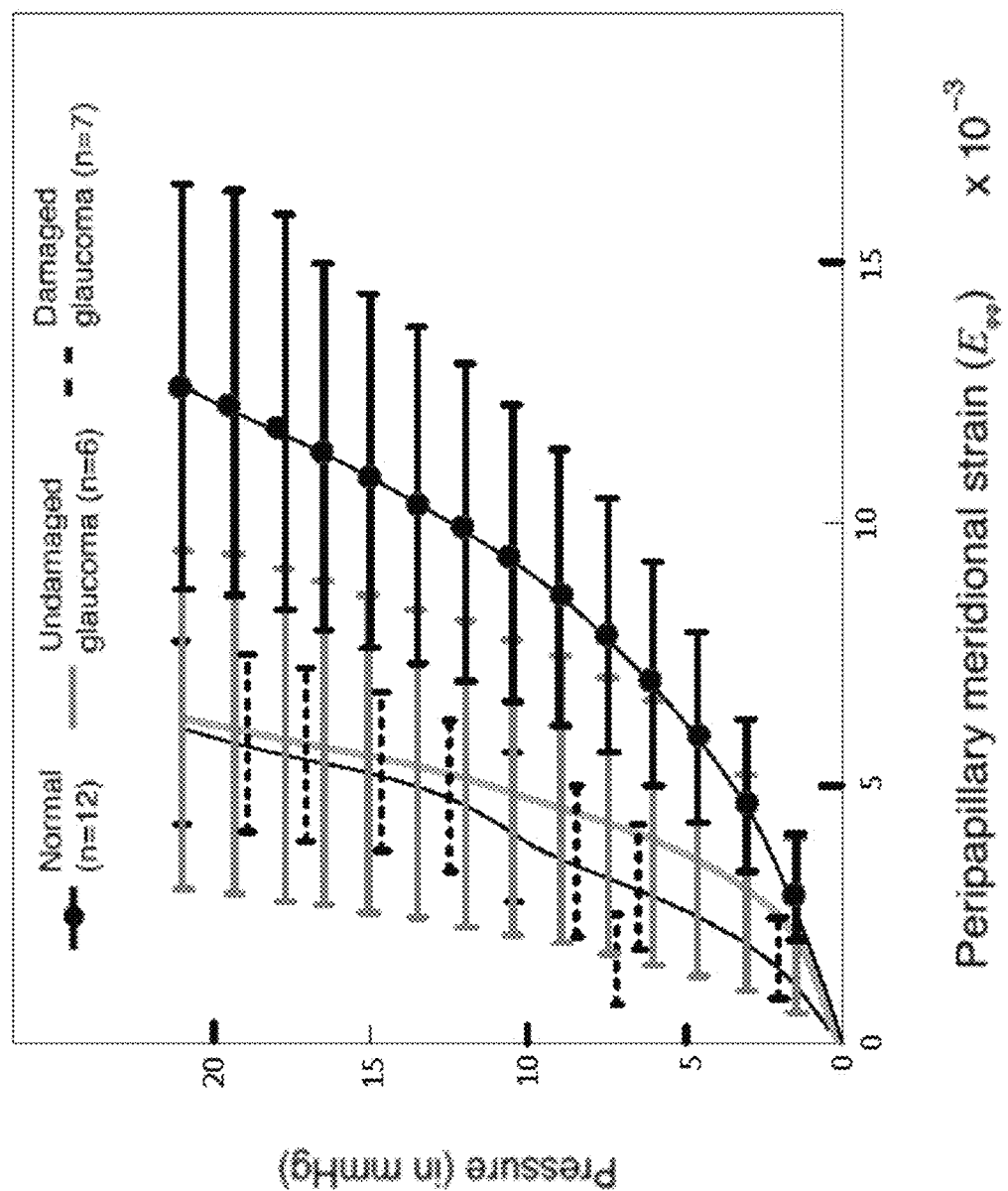
FIG. 17 is a graph showing the measured relationship between peripapillary meridional strain and intraocular pressure.

One embodiment envisions the use of a noncontact measurement of scleral strain that is capable of providing both accurate and convenient readings using well-vetted algorithms to extract appropriate spatial features with minimal equipment requirements. This can be achieved in a clinic setting via a system 1000 featuring portable tablet computing device 1002 containing a camera 1004, with additional optical elements 1006 (including, for example, a macro lens and a light source) to give the proper field of view with a very short working distance as shown in FIGS. 15 and 16. In this embodiment, targeted for use by ophthalmologist and optometrists, a patient's eye 1008 is imaged, (in one embodiment, the blood vessels in the sclera/conjunctiva directly adjacent to the limbus) while the patient's eye pressure is varied to two or more IOP levels. This can be achieved by changing the body position (standing up, sitting, laying down face up, laying down face down, etc), consuming caffeine or similar drug, using glaucoma medications known to reduce IOP, short exercise, or other means. From this in-otffice visit, clinician uses the novel system 1000 to document the patient's frontal scleral strain as a function of IOP, where the latter is measured using conventional means such as a Goldmann Applanation Tonometer. As IOP is increased, displacement of the natural features can be calculated from the tablet's imagery (e.g., a CMOS-based sensor or the like), creating a new metric—frontal scleral strain—that will track with IOP. In addition, for a given patient, how the relationship between scleral strain and IOP changes over time presents a third metric—ocular stiffness. The graph of FIG. 17 shows that ocular stiffness is statically different (stiffer) for patients suffering from Glaucoma.

To meet the need for consistent image resolution (so that image-to-image displacements can be calculated), a sequence of images is acquired while the working distance is slightly varied; the optimal focus point can be identified as representing the nominal lens-to-eye distance, with the known spatial resolution. One way of varying this is using an inflatable comfort pad 1010 wherein the pressure inside the pad is varied in a smooth fashion, such as sinusoidally with time. In another embodiment, the distance is varied by a cam residing inside the comfort pad 1010 that is connected to an electric motor. A disposable paper layer may placed on the pad 1010 and replaced with each use for patient comfort and cleanliness.

Any single image of the eye 1008 will result in a single displacement measurement, between a set of natural "fiducial" points on the eye. These fiducials are naturally occurring areas of visual pattern (such as blood vessels) that will be automatically extracted at an initial consultation (or with manual assistance).

The time-series of displacements over a short period of time is analyzed statistically to produce reliable and stable metrics. These are compared to displacements measured at the time of a known IOP reading to calculate the strain in the sclera. Customization can allow for the apparatus to be used at the correct angle each time, after a short "fitting session". The methods for utilizing the images and other calculations are substantially similar to those discussed above in relation to the wearable imaging system. Furthermore, a tablet screen 1012 allows for easy visualization of the patient's eye 1008 by the healthcare provider while utilizing the system 1000. In additional embodiments, the tablet screen 1012 may include overlay features or a split screen to aid the user in aligning the current (live) video image with previously captured videos, such as those from other pressure levels.

Although the foregoing has been described in detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention. Moreover, not all of the features, aspects and advantages described herein above are necessarily required to practice the present invention.

What is claimed is:

1. A method of monitoring eye health of a user, the method comprising:
   a) providing a scleral strain monitor comprising a wearable device comprising:
      i) one or more image sensors capable of capturing light in a near-infrared range,
      ii) a CPU,
      iii) a memory storage device,
      iv) one or more connecting wires,
      v) a power source; and
      vi) one or more illumination sources capable of emitting light at the near-infrared range, and capable of controlling illumination levels of an eye of the user;
   b) viewing a scleral stretch corresponding to changes in distance between two or more preselected target regions on or in a sclera of the eye of the user by the one or more image sensors recording at least two photographic images of the eye of the user at different times;
   c) transmitting the at least two photographic images of the eye of the user recorded by the one or more image sensors to the CPU, wherein the CPU determines the changes in distance between the two or more preselected target regions based on changes between the at least two photographic images;
   d) transmitting the at least two photographic images of the eye of the user received by the CPU or the changes in distance between the two or more preselected target regions determined by the CPU to the memory storage device;
   e) establishing a baseline level of scleral strain, wherein establishing the baseline level of scleral strain comprises modifying an intraocular pressure of the eye to a baseline level of pressure and recording the corresponding distance between the two or more preselected target regions in one of the at least two photographic images created in step b).

2. The method of claim 1, further comprising step f) calibrating the scleral strain monitor by modifying the intraocular pressure of the eye to another pressure, and recording the corresponding distance between the two or more preselected target regions in one of the at least two photographic images created in step b).

3. The method of claim 2, wherein the intraocular pressure of the eye of the user is modified by at least one method selected from the group consisting of: changing the user's body position, providing caffeine to the user and having the user perform exercise.

4. The method of claim 1, wherein the two or more preselected target regions are two separated symmetric implanted objects, two separated asymmetric implanted objects, two separated asymmetric objects or two distinct sclera regions.

5. The method of claim 4, wherein the two distinct sclera regions are areas of the sclera with distinct textures and with a measurable distance apart.

6. The method of claim 4, further comprising reducing depth-of-field errors by varying a distance between a lens of the one or more image sensors using a micromotor and using computer software to identify images captured at each extreme position relative to a depth of field and identifying an optimal focus point.

7. The method of claim 6, wherein sharpness of focus is used to identify the optimal focus point.

8. The method of claim 7, wherein the sharpness of focus is used to determine an optimal working distance between the lens and image sensor.

* * * * *